US012805757B2

(12) United States Patent
Gunturi et al.

(10) Patent No.: US 12,805,757 B2
(45) Date of Patent: Nov. 24, 2026

(54) CONTEXTUALIZATION OF SUBJECT PHYSIOLOGICAL SIGNAL USING MACHINE LEARNING

(71) Applicant: Covidien LP, Mansfield, MA (US)

(72) Inventors: Mridula Gunturi, Stratford-upon-Avon (GB); Paul S. Addison, Edinburgh (GB); Dean Montgomery, Edinburgh (GB)

(73) Assignee: Covidien LP, Mansfield, MA (US)

( * ) Notice: Subject to any disclaimer, the term of this patent is extended or adjusted under 35 U.S.C. 154(b) by 147 days.

(21) Appl. No.: 18/660,883

(22) Filed: May 10, 2024

(65) Prior Publication Data

US 2024/0374167 A1 Nov. 14, 2024

Related U.S. Application Data

(60) Provisional application No. 63/501,354, filed on May 10, 2023.

(51) Int. Cl.
*A61B 5/11* (2006.01)
*A61B 5/00* (2006.01)
(Continued)

(52) U.S. Cl.
CPC ........... *A61B 5/1128* (2013.01); *A61B 5/1118* (2013.01); *A61B 5/742* (2013.01);
(Continued)

(58) Field of Classification Search
CPC ..... A61B 5/1128; A61B 5/1118; A61B 5/742; A61B 2503/045; A61B 5/7267;
(Continued)

(56) References Cited

U.S. PATENT DOCUMENTS 5,107,845 A 4/1992 Guern et al.
5,408,998 A 4/1995 Mersch
(Continued)

FOREIGN PATENT DOCUMENTS

CA 2234191 A1 10/1998
CN 106725410 A 5/2017
(Continued)

OTHER PUBLICATIONS

Zaunseder , et al., "Spatio-temporal analysis of blood perfusion by imaging photoplethysmography", Progress in Biomedical Optics and Imaging, SPIE—International Society for Optical Engineering, vol. 10501, Feb. 20, 2018, 15 pages.
(Continued)

*Primary Examiner* — Abhishek Sarma
(74) *Attorney, Agent, or Firm* — Dymera IP, LLC

(57) ABSTRACT

Implementations described herein disclose a method of monitoring motion of a patient, the method includes receiving, using a processor, a video stream, the video stream comprising a sequence of images for at least a portion of a patient, dividing the video stream into a plurality of temporal video sequences, each of the temporal video sequences having a plurality of frames each being apart from each other, generating a matrix of depth difference frames, and determining a machine learning (ML) input feature matrix based on the matrix of depth difference frames.

20 Claims, 18 Drawing Sheets

(51) Int. Cl.
*G06T 5/70* (2024.01)
*G06T 7/246* (2017.01)
*G06T 7/579* (2017.01)

(52) U.S. Cl.
CPC ................ *G06T 5/70* (2024.01); *G06T 7/246* (2017.01); *G06T 7/579* (2017.01); *A61B 2503/045* (2013.01); *G06T 2207/10016* (2013.01); *G06T 2207/20032* (2013.01); *G06T 2207/20081* (2013.01); *G06T 2207/30004* (2013.01)

(58) Field of Classification Search
CPC ........... G06T 5/70; G06T 7/246; G06T 7/579; G06T 2207/10016; G06T 2207/20032; G06T 2207/20081; G06T 2207/30004; G06T 2207/10028; G06T 2207/20084; G06T 7/254
See application file for complete search history.

(56) References Cited

U.S. PATENT DOCUMENTS

| | | | |
|---|---|---|---|
| 5,704,367 | A | 1/1998 | Ishikawa et al. |
| 5,800,360 | A | 9/1998 | Kisner et al. |
| 5,995,856 | A | 11/1999 | Mannheimer et al. |
| 6,241,684 | B1 | 6/2001 | Amano et al. |
| 6,668,071 | B1 | 12/2003 | Minkin et al. |
| 6,920,236 | B2 | 7/2005 | Prokoski |
| 7,431,700 | B2 | 10/2008 | Aoki et al. |
| 7,558,618 | B1 | 7/2009 | Williams |
| 8,149,273 | B2 | 4/2012 | Liu et al. |
| 8,754,772 | B2 | 6/2014 | Horng et al. |
| 8,792,969 | B2 | 7/2014 | Bernal et al. |
| 8,971,985 | B2 | 3/2015 | Bernal et al. |
| 9,226,691 | B2 | 1/2016 | Bernal et al. |
| 9,282,725 | B2 | 3/2016 | Jensen-Jarolim et al. |
| 9,301,710 | B2 | 4/2016 | Mestha et al. |
| 9,402,601 | B1 | 8/2016 | Berger et al. |
| 9,436,984 | B2 | 9/2016 | Xu et al. |
| 9,443,289 | B2 | 9/2016 | Xu et al. |
| 9,504,426 | B2 | 11/2016 | Kyal et al. |
| 9,508,141 | B2 | 11/2016 | Khachaturian et al. |
| 9,607,138 | B1 | 3/2017 | Baldwin et al. |
| 9,662,022 | B2 | 5/2017 | Kyal et al. |
| 9,693,693 | B2 | 7/2017 | Farag et al. |
| 9,693,710 | B2 | 7/2017 | Mestha et al. |
| 9,697,599 | B2 | 7/2017 | Prasad et al. |
| 9,750,461 | B1 | 9/2017 | Telfort |
| 9,839,756 | B2 | 12/2017 | Klasek |
| 9,943,371 | B2 | 4/2018 | Bresch et al. |
| 10,213,540 | B2 | 2/2019 | Burbank et al. |
| 10,278,585 | B2 | 5/2019 | Ferguson et al. |
| 10,342,464 | B2 | 7/2019 | Niemeyer |
| 10,376,147 | B2 | 8/2019 | Wood et al. |
| 10,398,353 | B2 | 9/2019 | Addison et al. |
| 10,447,972 | B2 | 10/2019 | Patil |
| 10,489,912 | B1 | 11/2019 | Brailovskiy |
| 10,523,852 | B2 | 12/2019 | Tzvieli et al. |
| 10,588,779 | B2 | 3/2020 | Vorhees et al. |
| 10,589,916 | B2 | 3/2020 | Mcrae |
| 10,650,585 | B2 | 5/2020 | Kiely |
| 10,667,723 | B2 | 6/2020 | Jacquel et al. |
| 10,702,188 | B2 | 7/2020 | Addison et al. |
| 10,729,357 | B2 | 8/2020 | Larson et al. |
| 10,874,331 | B2 | 12/2020 | Kaiser et al. |
| 10,937,296 | B1 | 3/2021 | Kukreja et al. |
| 10,939,824 | B2 | 3/2021 | Addison et al. |
| 10,939,834 | B2 | 3/2021 | Khwaja et al. |
| 10,966,059 | B1 | 3/2021 | Dayal et al. |
| 11,311,252 | B2 | 4/2022 | Jacquel et al. |
| 11,315,275 | B2 | 4/2022 | Addison et al. |
| 11,317,828 | B2 | 5/2022 | Addison et al. |
| 11,350,850 | B2 | 6/2022 | Jacquel et al. |
| 11,484,208 | B2 | 11/2022 | Addison |
| 11,510,584 | B2 | 11/2022 | Addison et al. |
| 11,547,313 | B2 | 1/2023 | Addison et al. |
| 11,617,520 | B2 | 4/2023 | Addison et al. |
| 11,684,287 | B2 | 6/2023 | Addison et al. |
| 11,712,176 | B2 | 8/2023 | Addison et al. |
| 11,776,146 | B2 | 10/2023 | Addison et al. |
| 11,850,026 | B2 | 12/2023 | Levi et al. |
| 11,937,900 | B2 | 3/2024 | Addison et al. |
| 2002/0137464 | A1 | 9/2002 | Dolgonos et al. |
| 2004/0001633 | A1 | 1/2004 | Caviedes |
| 2004/0258285 | A1 | 12/2004 | Hansen et al. |
| 2005/0203348 | A1 | 9/2005 | Shihadeh et al. |
| 2007/0116328 | A1 | 5/2007 | Sablak et al. |
| 2008/0001735 | A1 | 1/2008 | Tran |
| 2008/0108880 | A1 | 5/2008 | Young et al. |
| 2008/0279420 | A1 | 11/2008 | Masticola et al. |
| 2008/0295837 | A1 | 12/2008 | Mccormick et al. |
| 2009/0024012 | A1 | 1/2009 | Li et al. |
| 2009/0141124 | A1 | 6/2009 | Liu et al. |
| 2009/0304280 | A1 | 12/2009 | Aharoni et al. |
| 2010/0210924 | A1 | 8/2010 | Parthasarathy et al. |
| 2010/0236553 | A1 | 9/2010 | Jafari et al. |
| 2010/0249630 | A1 | 9/2010 | Droitcour et al. |
| 2010/0324437 | A1 | 12/2010 | Freeman et al. |
| 2011/0144517 | A1 | 6/2011 | Cervantes |
| 2011/0150274 | A1 | 6/2011 | Patwardhan et al. |
| 2012/0065533 | A1 | 3/2012 | Carrillo et al. |
| 2012/0075464 | A1 | 3/2012 | Derenne et al. |
| 2012/0195473 | A1 | 8/2012 | De Haan et al. |
| 2012/0243797 | A1 | 9/2012 | Di Venuto Dayer et al. |
| 2013/0073312 | A1 | 3/2013 | Thompson et al. |
| 2013/0267873 | A1 | 10/2013 | Fuchs |
| 2013/0271591 | A1 | 10/2013 | Van Leest et al. |
| 2013/0272393 | A1 | 10/2013 | Kirenko et al. |
| 2013/0275873 | A1 | 10/2013 | Shaw et al. |
| 2013/0324830 | A1 | 12/2013 | Bernal et al. |
| 2013/0324876 | A1 | 12/2013 | Bernal et al. |
| 2014/0023235 | A1 | 1/2014 | Cennini et al. |
| 2014/0052006 | A1 | 2/2014 | Lee et al. |
| 2014/0053840 | A1 | 2/2014 | Liu |
| 2014/0073860 | A1 | 3/2014 | Urtti |
| 2014/0139405 | A1 | 5/2014 | Ribble et al. |
| 2014/0140592 | A1 | 5/2014 | Lasenby et al. |
| 2014/0235976 | A1 | 8/2014 | Bresch et al. |
| 2014/0267718 | A1 | 9/2014 | Govro et al. |
| 2014/0272860 | A1 | 9/2014 | Peterson et al. |
| 2014/0275832 | A1 | 9/2014 | Muehlsteff et al. |
| 2014/0276104 | A1 | 9/2014 | Tao et al. |
| 2014/0276130 | A1 | 9/2014 | Mirelman et al. |
| 2014/0330336 | A1 | 11/2014 | Errico et al. |
| 2014/0334697 | A1 | 11/2014 | Kersten et al. |
| 2014/0358017 | A1 | 12/2014 | Op Den Buijs et al. |
| 2014/0378810 | A1 | 12/2014 | Davis et al. |
| 2014/0379369 | A1 | 12/2014 | Kokovidis et al. |
| 2015/0003723 | A1 | 1/2015 | Huang et al. |
| 2015/0068069 | A1 | 3/2015 | Tran et al. |
| 2015/0094597 | A1 | 4/2015 | Mestha et al. |
| 2015/0131880 | A1 | 5/2015 | Wang et al. |
| 2015/0157269 | A1 | 6/2015 | Lisogurski et al. |
| 2015/0198707 | A1 | 7/2015 | Al-Alusi |
| 2015/0223731 | A1 | 8/2015 | Sahin |
| 2015/0238150 | A1 | 8/2015 | Subramaniam |
| 2015/0265187 | A1 | 9/2015 | Bernal et al. |
| 2015/0282724 | A1 | 10/2015 | Mcduff et al. |
| 2015/0286779 | A1 | 10/2015 | Bala et al. |
| 2015/0301590 | A1 | 10/2015 | Furst et al. |
| 2015/0317814 | A1 | 11/2015 | Johnston et al. |
| 2015/0379370 | A1 | 12/2015 | Clifton et al. |
| 2016/0000335 | A1 | 1/2016 | Khachaturian et al. |
| 2016/0049094 | A1 | 2/2016 | Gupta et al. |
| 2016/0082222 | A1 | 3/2016 | Garcia Molina et al. |
| 2016/0140828 | A1 | 5/2016 | Deforest |
| 2016/0143598 | A1 | 5/2016 | Rusin et al. |
| 2016/0151022 | A1 | 6/2016 | Berlin et al. |
| 2016/0156835 | A1 | 6/2016 | Ogasawara et al. |
| 2016/0174887 | A1 | 6/2016 | Kirenko et al. |
| 2016/0210747 | A1 | 7/2016 | Hay et al. |
| 2016/0235344 | A1 | 8/2016 | Auerbach |
| 2016/0310084 | A1 | 10/2016 | Banerjee et al. |

(56) References Cited

U.S. PATENT DOCUMENTS

| | | | |
|---|---|---|---|
| 2016/0317041 | A1 | 11/2016 | Porges et al. |
| 2016/0345931 | A1 | 12/2016 | Xu et al. |
| 2016/0367186 | A1 | 12/2016 | Freeman et al. |
| 2017/0007342 | A1 | 1/2017 | Kasai et al. |
| 2017/0007795 | A1 | 1/2017 | Pedro et al. |
| 2017/0055877 | A1 | 3/2017 | Niemeyer |
| 2017/0065484 | A1 | 3/2017 | Addison et al. |
| 2017/0071516 | A1 | 3/2017 | Bhagat et al. |
| 2017/0095215 | A1 | 4/2017 | Watson et al. |
| 2017/0095217 | A1 | 4/2017 | Hubert et al. |
| 2017/0119340 | A1 | 5/2017 | Nakai et al. |
| 2017/0147772 | A1 | 5/2017 | Meehan et al. |
| 2017/0164904 | A1 | 6/2017 | Kirenko |
| 2017/0172434 | A1 | 6/2017 | Amelard et al. |
| 2017/0173262 | A1 | 6/2017 | Veltz |
| 2017/0238805 | A1 | 8/2017 | Addison et al. |
| 2017/0238842 | A1 | 8/2017 | Jacquel et al. |
| 2017/0311887 | A1 | 11/2017 | Leussler et al. |
| 2017/0319114 | A1 | 11/2017 | Kaestle |
| 2018/0042486 | A1 | 2/2018 | Yoshizawa et al. |
| 2018/0042500 | A1 | 2/2018 | Liao et al. |
| 2018/0049669 | A1 | 2/2018 | Vu et al. |
| 2018/0053392 | A1 | 2/2018 | White et al. |
| 2018/0104426 | A1 | 4/2018 | Oldfield et al. |
| 2018/0106897 | A1 | 4/2018 | Shouldice et al. |
| 2018/0169361 | A1 | 6/2018 | Dennis et al. |
| 2018/0217660 | A1 | 8/2018 | Dayal et al. |
| 2018/0228381 | A1 | 8/2018 | Leboeuf et al. |
| 2018/0303351 | A1 | 10/2018 | Mestha et al. |
| 2018/0310844 | A1 | 11/2018 | Tezuka et al. |
| 2018/0325420 | A1 | 11/2018 | Gigi |
| 2018/0333050 | A1 | 11/2018 | Greiner et al. |
| 2018/0333102 | A1 | 11/2018 | De Haan et al. |
| 2018/0352150 | A1 | 12/2018 | Purwar et al. |
| 2019/0050985 | A1 | 2/2019 | Den Brinker et al. |
| 2019/0133499 | A1 | 5/2019 | Auerbach |
| 2019/0142274 | A1 | 5/2019 | Addison et al. |
| 2019/0199970 | A1 | 6/2019 | Greiner et al. |
| 2019/0209046 | A1 | 7/2019 | Addison et al. |
| 2019/0209083 | A1 | 7/2019 | Wu et al. |
| 2019/0307365 | A1 | 10/2019 | Addison et al. |
| 2019/0311101 | A1 | 10/2019 | Nienhouse |
| 2019/0320974 | A1 | 10/2019 | Alzamzmi et al. |
| 2019/0343480 | A1 | 11/2019 | Shute et al. |
| 2019/0380599 | A1 | 12/2019 | Addison et al. |
| 2019/0380807 | A1 | 12/2019 | Addison et al. |
| 2020/0046302 | A1 | 2/2020 | Jacquel et al. |
| 2020/0187827 | A1 | 6/2020 | Addison et al. |
| 2020/0202154 | A1 | 6/2020 | Wang et al. |
| 2020/0205734 | A1 | 7/2020 | Mulligan et al. |
| 2020/0237225 | A1 | 7/2020 | Addison et al. |
| 2020/0242790 | A1 | 7/2020 | Addison et al. |
| 2020/0250406 | A1 | 8/2020 | Wang et al. |
| 2020/0253560 | A1 | 8/2020 | De Haan |
| 2020/0279464 | A1 | 9/2020 | Llewelyn |
| 2020/0289024 | A1 | 9/2020 | Addison et al. |
| 2020/0329976 | A1 | 10/2020 | Chen et al. |
| 2020/0409383 | A1 | 12/2020 | Maunder |
| 2021/0068670 | A1 | 3/2021 | Redtel |
| 2021/0142874 | A1 | 5/2021 | Llewelyn |
| 2021/0153746 | A1 | 5/2021 | Addison et al. |
| 2021/0201517 | A1 | 7/2021 | Yang et al. |
| 2021/0233631 | A1 | 7/2021 | Llewelyn |
| 2021/0235992 | A1 | 8/2021 | Addison |
| 2021/0295662 | A1 | 9/2021 | Bugbee et al. |
| 2021/0313075 | A1 | 10/2021 | Mc Namara et al. |
| 2022/0211296 | A1 | 7/2022 | Addison et al. |
| 2022/0331028 | A1 | 10/2022 | Sternitzke et al. |
| 2023/0122367 | A1 | 4/2023 | Tesar |

FOREIGN PATENT DOCUMENTS

| | | | |
|---|---|---|---|
| CN | 111728602 | A | 10/2020 |
| CN | 112233813 | A | 1/2021 |
| DE | 19741982 | A1 | 10/1998 |
| EP | 2793189 | B1 | 11/2016 |
| EP | 2428162 | B1 | 8/2017 |
| EP | 3207862 | A1 | 8/2017 |
| EP | 3207863 | A1 | 8/2017 |
| EP | 3384827 | A1 | 10/2018 |
| EP | 2772828 | B1 | 1/2019 |
| JP | 2004173010 | A | 6/2004 |
| JP | 2004283373 | A | 10/2004 |
| JP | 3744778 | B2 | 12/2005 |
| JP | 2009544080 | A | 12/2009 |
| JP | 2011130996 | A | 7/2011 |
| KR | 101644843 | B1 | 8/2016 |
| RS | 20120373 | A1 | 4/2014 |
| WO | 2004100067 | A2 | 11/2004 |
| WO | 2005079658 | A2 | 9/2005 |
| WO | 2010034107 | A1 | 4/2010 |
| WO | 2010036653 | A1 | 4/2010 |
| WO | 2015059700 | A1 | 4/2015 |
| WO | 2015078735 | A1 | 6/2015 |
| WO | 2015110859 | A1 | 7/2015 |
| WO | 2016065411 | A1 | 5/2016 |
| WO | 2016178141 | A1 | 11/2016 |
| WO | 2016209491 | A1 | 12/2016 |
| WO | 2017060463 | A1 | 4/2017 |
| WO | 2017089139 | A1 | 6/2017 |
| WO | 2017100188 | A2 | 6/2017 |
| WO | 2017144934 | A1 | 8/2017 |
| WO | 2018042376 | A1 | 3/2018 |
| WO | 2019094893 | A1 | 5/2019 |
| WO | 2019135877 | A1 | 7/2019 |
| WO | 2019240991 | A1 | 12/2019 |
| WO | 2020033613 | A1 | 2/2020 |
| WO | 2021044240 | A1 | 3/2021 |

OTHER PUBLICATIONS

Zhou, J. , et al., “Maximum parsimony analysis of gene copy No. changes in tumor phylogenetics”, 15th International Workshop on Algorithms in Bioinformatics WABI 2015, Atlanta, USA, 2015, pp. 108-120, 13 pages.

Kwon, Sungjun , et al., “Validation of heart rate extraction using video imaging on a built-in camera system of a smartphone”, 34th Annual International Conference of the IEEE Embs, San Diego, CA, USA, Aug. 28-Sep. 1, 2012, pp. 2174-2177, 4 pages.

Lai, C.J. , et al., “Heated humidified high-flow nasal oxygen prevents intraoperative body temperature decrease in non-intubated thoracoscopy”, Journal of Anesthesia, Oct. 15, 2018, 8 pages.

Lawrence, E. , et al., “Data Collection, Correlation and Dissemination of Medical Sensor information in a WSN”, IEEE 2009 Fifth International Conference on Networking and Services, 978-0-7695-3586-9/09, Apr. 20, 2009, pp. 402-408, 7 pages.

Li , et al., “A Non-Contact Vision-Based System for Respiratory Rate Estimation”, IEEE 978-1-4244-7929-0/14, 2014, pp. 2119-2122, 4 pages.

Liu, H. , et al., “A Novel Method Based on Two Cameras for Accurate Estimation of Arterial Oxygen Saturation”, BioMedical Engineering Online, vol. 14, No. 52, 2015, 18 pages.

Liu, Xinyi , et al., “An Image Captioning Method for Infant Sleeping Environment Diagnosis”, Springer International Publishing, May 15, 2019, pp. 18-26, 9 pages.

Liu, S. , et al., “In-bed pose estimation: Deep learning with shallow dataset. IEEE journal of translational engineering in health and medicine”, IEEE Journal of Translational Engineering in Health and Medicine, No. 7, 2019, pp. 1-12, 12 pages.

Liu, C. , et al., “Motion Magnification”, ACM Transactions on Graphics (TOG), vol. 24, No. 3, 2005, pp. 519-526, 8 pages.

LV, et al., “Class Energy Image Analysis for Video Sensor-Based Gait Recognition: A Review”, Sensors, No. 15, 2015, pp. 932-964, 33 pages.

Mcduff, Daniel J., et al., “A Survey of Remote Optical Photoplethysmographic Imaging Methods”, IEEE 987-1-4244-0270-1/15, 2015, pp. 6398-6404, 7 pages.

Mestha, L.K. , et al., “Towards Continuous Monitoring of Pulse Rate in Neonatal Intensive Care Unit with a Webcam”, Proc. of 36th

(56) References Cited

OTHER PUBLICATIONS

Annual Int. Conf. of the IEEE Engineering in Medicine and Biology Society, Chicago, IL, 2014, pp. 3817-3820, 4 pages.
Mukherjee, S. , et al., "Patient health management system using e-health monitoring architecture", IEEE, International Advance Computing Conference (IACC), 978-1-4799-2572-8/14, Feb. 21, 2014, pp. 400-405, 6 pages.
Nguyen , et al., "3D shape, deformation and vibration measurements using infrared Kinect sensors and digital image correlation", Applied Optics, vol. 56, No. 32, Nov. 10, 2017, 8 pages.
Ni , et al., "RGBD-Camera Based Get-Up Event Detection for Hospital Fall Prevention", Acoustics, Speech and Signal Processing (ICASSP) 2012 IEEE International Conf., Mar. 2012, pp. 1405-1408, 6 pages.
Nisar , et al., "Contactless heart rate monitor for multiple persons in a video", IEEE International Conference on Consumer Electronics-Taiwan (Icce-Tw), XP03291229 [Retreived on Jul. 25, 2016], May 27, 2016, 2 pages.
Pereira, C. , et al., "Noncontact Monitoring of Respiratory Rate in Newborn Infants Using Thermal Imaging", IEEE Transactions on Biomedical Engineering, Aug. 23, 2018, 10 pages.
Poh , et al., "Advancements in Noncontact, Multiparameter Physiological Measurements Using a Webcam", IEEE Transactions on Biomedical Engineering, vol. 58, No. 1, Jan. 2011, pp. 7-11, 5 pages.
Poh , et al., "Non-contact, automated cardiac pulse measurements using video imaging and blind source separation", OPT. Express 18, 2010, pp. 10762-10774, 14 pages.
Povsic, Klemen , et al., "Real-Time 3D visualization of the thoraco-abdominal surface during breathing with body movement and deformation extraction", Physiological Measurement, vol. 36, No. 7, May 28, 2015, pp. 1497-1516, 22 pages.
Prochazka, et al., "Microsoft Kinect Visual and Depth Sensors for Breathing and Heart Rate Analysis", Senors, vol. 16, No. 7, Jun. 28, 2016, 11 pages.
Rajan, V. , et al., "Clinical Decision Support for Stroke using Multiview Learning based Models for NIHSS Scores", PAKDD 2016 Workshop: Predictive Analytics in Critical Care (PACC), Auckland, New Zealand, 2016, pp. 190-199, 10 pages.
Rajan, V. , et al., "Dependency Clustering of Mixed Data with Gaussian Mixture Copulas", 25th International Joint Conference on Artificial Intelligence IJCAI, New York, USA, 2016, pp. 1967-1973, 7 pages.
Reisner, A. , et al., "Utility of the Photoplethysmogram in Circulatory Monitoring", American Society of Anesthesiologist, May 2008, pp. 950-958, 9 pages.
Reyes, B.A., et al., "Tidal vol. and Instantaneous Respiration Rate Estimation using a Volumetric Surrogate Signal Acquired via a Smartphone Camera", IEEE Journal of Biomedical and Health Informatics, vol. 21(3), Feb. 25, 2016, pp. 764-777, 15 pages.
Rezaei, Mahdi , et al., "DeepSOCIAL: Social Distancing Monitoring and Infection Risk Assessment in COVID-19 Pandemic", Applied Sciences, vol. 10, 7514, Oct. 26, 2020, pp. 1-29, 29 pages.
Rougier, Caroline , et al., "Robust Video Surveillance for Fall Detection Based on Human Shape Deformation", IEEE Transactions on Circuits and Systems for Video Technology, vol. 21, No. 5, May 2011, pp. 611-622, 12 pages.
Rubinstein, M , "Analysis and Visualization of Temporal Variations in Video", Department of Electrical Engineering and Computer Science, Massachusetts Institute of Technology, Feb. 2014, 118 pages.
Sathyamoorthy, Adarsh Jagan, et al., "COVID-Robot: Monitoring Social Distancing Constraints in Crowded Scenarios", Aug. 21, 2020, pp. 1-11, 11 pages.
Scalise, Lorenzo , et al., "Heart rate measurement in neonatal patients using a webcamera", Department of Industrial Engineering and Mathematical Science, Italy, 978-1-4673-0882-3/12, EEE, 2012, 4 pages.
Schaerer, J. , et al., "Multi-dimensional respiratory motion tracking from markerless optical surface imaging based on deformable mesh registration", Physics in Medicine and Biology, vol. 57, No. 2, Dec. 14, 2011, pp. 357-373, 18 pages.
Sengupta, A. , et al., "A Statistical Model for Stroke Outcome Prediction and Treatment Planning", 38th Annual International Conference of the IEE Engineering in Medicine and Biology (Society IEEE EMBC2016), Orlando, USA, 2016, pp. 2516-2519, 4 pages.
Shah, Nitin , et al., "Performance of three new-generation pulse oximeters during motion and low perfursion in volunteers", Journal of Clinical Anesthesia, No. 24, 2012, pp. 385-391, 7 pages.
Shao, Dangdang , et al., "Noncontact Monitoring Breathing Pattern, Exhalation Flow Rate and Pulse Transit Time", EEE Transactions on Biomedical Engineering, vol. 61, No. 11, Nov. 2014, pp. 2760-2767, 8 pages.
Shrivastava, H. , et al., "Classification with Imbalance: A Similarity-based Method for Predicting Respiratory Failure", IEEE International Conference on Bioinformatics and Biomedicine (IEEE BIBM2015), Washington, DC,USA, 2015, pp. 707-714, 8 pages.
Sokooti, Hess , et al., "Hierarchical Prediction of Registration Misalignment Using a Convolutional LSTM: Application to Chest CT Scans", IEEE Access, IEEE, USA, vol. 9, Apr. 20, 2021, 62008-62020, 13 pages.
Srinivas, J. , et al., "A Mutual Authentication Framework for Wireless Medical Sensor Networks", Journal of Medical Systems, 41:80, 2017, pp. 1-19, 19 pages.
Sun, Yu , et al., "Motion-compensated noncontact imaging photoplethysmography to monitor cardiorespiratory status during exercise", Journal of Biomedical Optics, vol. 16, No. 7, Jul. 1, 2011, 10 pages.
Sun, Yu , et al., "Noncontact imaging photoplethysmography to effectively access pulse rate variability", Journal of Biomedical Optics, vol. 18(6), Jun. 2013, 10 pages.
Tamura , et al., "Wearable Photoplethysmographic Sensors-Past & Present", Electronics, vol. 3, 2014, pp. 282-302, 21 pages.
Tarassenko, L. , et al., "Non-contact video-based vital sign monitoring using ambient light and auto-regressive models", Institute of Physics and Engineering in Medicine, vol. 35, 2014, pp. 807-831, 26 pages.
Teichmann, D. , et al., "Non-Contact monitoring techniques-Principles and applications", In Proc. of IEEE International Conference of the Engineering in Medicine and Biology Society (EMBC), San Diego, CA, 2012, pp. 1302-1305, 4 pages.
Transue, S. , et al., "Real-time Tidal vol. Estimation using Iso-surface Reconstruction", 2016 IEEE First International Conference on Connected Health: Applications, Systems and Engineering Technologies (CHASE), Jun. 27, 2016, pp. 209-218, 10 pages.
Verkruysee, Wim , et al., "Calibration of Contactless Pulse Oximetry", Anesthesia & Analgesia, vol. 124, No. 1, Jan. 2017, pp. 136-145, 10 pages.
Mllarroel, Mauricio , et al., "Continuous non-contact vital sign monitoring in neonatal intensive care unit", Healthcare Technology Letters, vol. 1, Issue 3, 2014, pp. 87-91, 5 pages.
Wadhwa, N. , et al., "Phase-Based Video Motion Processing", MIT Computer Science and Artificial Intelligence Lab, Jul. 2013, 9 pages.
Wadhwa, N. , et al., "Riesz pyramids for fast phase-based video magnification", In Proc. of IEEE International Conference on Computational Photography (ICCP), Santa Clara, CA, 2014, 10 pages.
Wang, W. , et al., "Exploiting spatial redundancy of image sensor for motion robust rPPG", IEEE Transactions on Biomedical Engineering, vol. 62, No. 2, 2015, pp. 415-425, 11 pages.
Wu, H.Y. , et al., "Eulerian video magnifcation for revealing subtle changes in the world", ACM Transactions on Graphics (TOG), vol. 31, No. 4, 2012, pp. 651-658, 8 pages.
Wulbrand, H. , et al., "Submental and diaphragmatic muscle activity during and at resolution of mixed and obstructive apneas and cardiorespiratory arousal in preterm infants", Pediatric Research, No. 38(3), 1995, pp. 298-305, 9 pages.
Yu, M.C. , et al., "Noncontact Respiratory Measurement of vol. Change Using Depth Camera", 2012 Annual International Confer-

(56) References Cited

OTHER PUBLICATIONS ence of the IEEE Engeineering in Medicine and Biology Society, Aug. 28, 2012, pp. 2371-2374, 4 pages.
"International Search Report and Written Opinion", International Application No. PCT/US24/28848, Sep. 6, 2024, 7pgs.
"European Search Report", European Application No. 17156334.9, Applicant: Covidien LP, Aug. 23, 2017, 10 pages.
"European Search Report", European Patent Application No. 17156337.2, Applicant: Covidien LP, Aug. 23, 2017, 10 pages.
"International Search Report and Written Opinion", International Application No. PCT/US2021/015669, Apr. 12, 2021, 15 pages.
"International Search Report and Written Opinion", International Application No. PCT/US2018/060648, Jan. 28, 2019, 17 pages.
"International Search Report and Written Opinion", International Application No. PCT/US2018/065492, Mar. 8, 2019, 12 pages.
"International Search Report and Written Opinion", International Application No. PCT/US2019/035433, Nov. 11, 2019, 17 pages.
"International Search Report and Written Opinion", International Application No. PCT/US2019/045600, Oct. 23, 2019, 19 pages.
"Invitation to Pay Additional Fees and Partial International Search Report", International Application No. PCT/US2019/035433, Sep. 13, 2019, 16 pages.
"Medical Electrical Equipment, Part 2-61: Particular requirements for basic safety and essential performance of pulse oximeter equipment", BSI Standards Publication, BS EN ISO 80601-2-61, 2011, 98 pages.
Aarts, Lonneke A.M., et al., "Non-contact heart rate monitoring utilizing camera photoplethysmography in neonatal intensive care unit—A Pilot Study", Early Human Development 89, 2013, pp. 943-948, 6 pages.
Abbas, A.K. , et al., "Neonatal non-contact respiratory monitoring based on real-time infrared thermography", Biomed. Eng. Online, vol. 10, No. 93, 2011, 17 pages.
Addison, Paul S., "A Review of Signal Processing Used in the Implementation of the Pulse Oximetry Photoplethysmographic Fluid Responsiveness Parameter", International Anesthesia Research Society, vol. 119, No. 6, Dec. 2014, pp. 1293-1306, 14 pages.
Addison, Paul S., et al., "Developing an algorithm for pulse oximetry derived respirator rate (RRoxi): a healthy volunteer study", J Clin comput, No. 26, 2012, pp. 45-51, 7 pages.
Addison, Paul S., et al., "Pulse oximetry-derived respiratory rate in general care floor patients", J. Clin Monit Comput, No. 29, 2015, pp. 113-120, 8 pages.
Addison, P.S. , et al., "Video-based Heart Rate Monitoring across a Range of Skin Pigmentations during an Acute Hypoxic Challenge", J Clin Monit Comput, vol. 9, Nov. 9, 2017, 15 pages.
Al-Naji, Ali , et al., "Real Time Apnoea Monitoring of Children Using the Microsoft Kinect Sensor: A Pilot Study", Sensors, 17(286), Feb. 3, 2017, 15 pages.
Amazon , "Dockem Koala Tablet Wall Mount Dock for ipad Air/Mini/Pro, Samsung Galaxy Tab/Note, Nexus 7/10, and More (Black Brackets, Screw-in Version)", https://www.amazon.com/Tablet-Dockem-Samsung-Brackets-Version-dp/B00JV75FC6?th=1, First available Apr. 22, 2014, viewed on Nov. 16, 2021, Apr. 22, 2014, 4 pages.
Amelard , et al., "Non-contact transmittance photoplethysmographic imaging (PPGI) for long-distance cardiovascular monitoring", ResearchGate, XP055542534 [Retrieved online Jan. 15, 2019], Mar. 23, 2015, pp. 1-13, 14 pages.
Armanian, A. M. , "Caffeine administration to prevent apnea in very premature infants", Pediatrics & Neonatology, 57 (5), 2016, pp. 408-412, 5 pages.
Barone, S, et al., "Computer-aided modelling of three-dimensional maxillofacial tissues through multi-modal imaging", Proceedings of the Institution of Mechanical Engineers, Journal of Engineering in Medicine, Part H vol. 227, No. 2, Feb. 1, 2013, 1 page.
Barone, S, et al., "Creation of 3D Multi-body Orthodontic Models by Using Independent Imaging Sensors", Senros MDPI AG Switzerland, vol. 13, No. 2, Jan. 1, 2013, pp. 2033-2050, 18 pages.
Bartula, M. , et al., "Camera-based System for Sontactless Monitoring of Respiration", 2013 35th Annual International Conference of the IEEE Engineering in Medicine and Biology Society (EMBC), Jul. 3, 2013, pp. 2672-2675, 4 pages.
Bhattacharya, S. , et al., "A Novel Classification Method for Predicting Acute Hypotensive Episodes in Critical Care", 5th ACM Conference on Bioinformatics, Computational Bilogy and Health Informatics (ACM-BCB 2014), Newport Beach, USA, 2014, 10 pages.
Bhattacharya, S. , et al., "Unsupervised learning using Gaussian Mixture Copula models", 21st International Conference on Computational Statistics (COMPSTAT 2014), Geneva, Switzerland, 2014, pp. 523-530, 8 pages.
Bickler, Philip E., et al., "Factors Affecting the Performance of 5 Cerebral Oximeters During Hypoxia in Healthy Volunteers", Society for Technology in Anesthesia, vol. 117, No. 4, Oct. 2013, pp. 813-823, 11 pages.
Bousefsaf, Frederic , et al., "Continuous wavelet filtering on webcam photoplethysmographic signals to remotely assess the instantaneous heart rate", Biomedical Signal Processing and Control 8, 2013, pp. 568-574, 7 pages.
Bruser, C. , et al., "Adaptive Beat-to-Beat Heart Rate Estimation in Ballistocardiograms", IEEE Transactions Information Technology in Biomedicine, vol. 15, No. 5, Sep. 2011, pp. 778-786, 9 pages.
Cennini, Giovanni , et al., "Heart rate monitoring via remote photoplethysmography with motion artifacts reduction", Optics Express, vol. 18, No. 5, Mar. 1, 2010, pp. 4867-4875, 9 pages.
Colantonio, S. , et al., "A smart mirror to promote a healthy lifestyle", Biosystems Engineering. vol. 138, Innovations in Medicine and Healthcare, Oct. 2015, pp. 33-43, 11 pages.
Cooley , et al., "An Alorithm for the Machine Calculation of Complex Fourier Series", Aug. 17, 1964, pp. 297-301, 5 pages.
Di Fiore, J.M. , et al., "Intermittent hypoxemia and oxidative stress in preterm infants", Respiratory Physiology & Neurobiology, No. 266, 2019, pp. 121-129, 25 pages.
Fei, J. , et al., "Thermistor at a distance: unobtrusive measurement of breathing", IEEE Transactions on Biomedical Engineering, vol. 57, No. 4, 2010, pp. 968-998, 11 pages.
Feng, Litong , et al., "Dynamic ROI based on K-means for remote photoplethysmography", IEE International Conference on Accoustics, Speech and Signal Processing (ICASSP), Apr. 2015, pp. 1310-1314, 5 pages.
Fischer , et al., "ReMoteCare: Health Monitoring with Streaming Video", OCMB '08, 7th International Conference on Mobile Business, IEEE, Piscataway, NJ,, Jul. 7, 2008, pp. 280-286.
George , et al., "Respiratory Rate Measurement From PPG Signal Using Smart Fusion Technique", International Conference on Engineering Trends and Science & Humanities (ICETSH-2015), 2015, 5 pages.
Goldman, L.J. , "Nasal airflow and thoracoabdominal motion in children using infrared thermographic video processing", Pediatric Pulmonology, vol. 47, No. 5, 2012, pp. 476-486, 11 pages.
Grimm, T. , et al., "Sleep position classification from a depth camera using bed aligned maps", 23rd International Conference on Pattern Recognition (ICPR), Dec. 2016, pp. 319-324, 6 pages.
Gsmarena , "Apple iPad Pro 11 (2018)", https://www.gsmarena.com/apple_ipad_pro_11_(2018)-9386.pjp, viewed on Nov. 16, 2021, 1 page.
Guazzi, Alessandro R., et al., "Non-contact measurement of oxygen saturation with an RGB camera", Biomedical Optics Express, vol. 6, No. 9, Sep. 1, 2015, pp. 3320-3338, 19 pages.
Han, J. , et al., "Visible and infrared image registration in man-made environments employing hybrid visuals features", Pattern Recognition Letters, vol. 34, No. 1, 2013, pp. 42-51, 10 pages.
Harte, James M., et al., "Chest wall motion analysis in healthy volunteers and adults with cystic fibrosis using a novel Kinect-based motion tracking system", Medical & Biological Engineering & Computing, 54(11), Feb. 13, 2016, pp. 1631-1640, 11 pages.
Huddar, V. , et al., "Predicting Postoperative Acute Respiratory Failure in Critical Care using Nursing Notes and Physiological Signals", 36th Annual International Conference of IEEE Engineering in Medicine and Biology Society (IEEE EMBC 2014), Chicago, USA, 2014, pp. 2702-2705, 4 pages.

(56) References Cited

OTHER PUBLICATIONS

Hyvarinen, A. , et al., "Independent Component Analysis: Algorithms and Applications", Neural Networks, vol. 13, No. 4, 2000, pp. 411-430, 31 pages.
Javadi, M. , et al., "Diagnosing Pneumonia in Rural Thailand: Digital Cameras versus Film Digitizers for Chest Radiograph Teleradiology", International Journal of Infectious Disease, 10(2), Mar. 2006, pp. 129-135, 7 pages.
Jopling, M. W., et al., "Issues in the Laboratory Evaluation of Pulse Oximeter Performance", Anesth. Analg., No. 94, 2002, pp. S62-S68, 7 pages.
Kastle, Siegfried W., et al., "Determining the Artifact Sensitivity of Recent Pulse Oximeters During Laboratory Benchmarking", Journal of Clinical Monitoring and Computing, vol. 16, No. 7, 2000, pp. 509-552, 14 pages.
Klaessens, J.H.G.M. , et al., "Non-invasive skin oxygenation imaging using a multi-spectral camera system: Effectiveness of various concentration algorithms applied on human skin", Proc. of SPIE, vol. 7174 717408-1, 2009, 14 pages.
Kong, Lingqin , et al., "Non-contact detection of oxygen saturation based on visible light imaging device using ambient light", Optics Express, vol. 21, No. 15, Jul. 29, 2013, pp. 17646-17471, 8 pages.
Kortelainen, J.M. , et al., "Sleep staging based on signals acquired through bed sensor", IEEE Transactions on Informational Technology in Biomedicine, vol. 14, No. 3, May 2010, pp. 776-785, 10 pages.
Kumar, M. , et al., "Distance PPG: Robust non-contact vital signs monitoring using a camera", Biomedical Optics Express, vol. 6, No. 5, May 1, 2015, 24 pages.

CONTEXTUALIZATION OF SUBJECT PHYSIOLOGICAL SIGNAL USING MACHINE LEARNING

CROSS-REFERENCE TO RELATED APPLICATIONS

The present application claims benefit of priority to U.S. Provisional Patent Application No. 63/501,354, entitled "CONTEXTUALIZATION OF SUBJECT PHYSIOLOGICAL SIGNAL USING MACHINE LEARNING" and filed on May 10, 2023, which is specifically incorporated by reference herein for all that it discloses or teaches.

BACKGROUND

There is a need in the medical community to determine neonatal motion and/or activity for a number of reasons including to monitor relative neonatal activity over time which may correlate with disease state and/or over or under sedation and to help mitigate the effect of motion on physiological signals and their derived parameters (e.g. respiratory rate from the Transthoracic Impedance (TTI) signal). A range of depth sensing technologies are available to determine various physiological and contextual parameters, including respiration rate, tidal volume, minute volume, effort to breathe, activity, presence in bed, etc., that may be useful in detecting neonatal motion and/or activity. Specifically, video (RGB) and depth-sensing cameras have enormous potential to provide non-contact methods for the determination of physiological parameters.

SUMMARY

Implementations described herein disclose a method of monitoring motion of a patient, the method includes receiving, using a processor, a video stream, the video stream comprising a sequence of images for at least a portion of a patient, dividing the video stream into a plurality of temporal video sequences, each of the temporal video sequences having a plurality of frames each being apart from each other, generating a matrix of depth difference frames, and determining a machine learning (ML) input feature matrix based on the matrix of depth difference frames.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

Other implementations are also described and recited herein.

BRIEF DESCRIPTIONS OF THE DRAWINGS

A further understanding of the nature and advantages of the present technology may be realized by reference to the figures, which are described in the remaining portion of the specification.

FIG. 1 illustrates a non-contact subject monitoring system that can be used for contextualization of subject physiological signals using machine learning.

FIG. 2 indicates an example of a depth video image of a neonatal patient.

DETAILED DESCRIPTIONS

Neonatal care typically requires constant or near constant monitoring of various physiological parameters of neonatal patients. For example, when in the ICU, various physiological parameters such as ECG, oxygen saturation levels, respiratory rate, etc., of a neonatal patient are typically monitored on a continuous basis. Any abnormal changes in such physiological parameters may generate an alarm or require immediate attention of a caretaker. However, sometimes, changes to such physiological parameters may be simply the result of movement or motion by the neonatal patient. Therefore, it is useful if a display of a neonatal physiological parameter is modified to indicate presence of a motion of the neonate.

The technology disclosed herein provides a method of monitoring motion using our touchless monitoring system which involves a machine learning (ML) model. Specifically, the system disclosed herein may be used to monitor motion and activity as a physiological parameter from the touchless system, or it may be used to monitor motion so that its effect on the measurement of a physiological parameter may be mitigated. For the latter, this may be a physiological parameter from the touchless system including respiratory rate or it may be from another device, such as oxygen saturation from a pulse oximeter, heart rate from an ECG, or respiration from any other device. Such contextualization of respiratory rate using the proposed motion flag may significantly enhance the interpretation of this parameter in the neonatal intensive care unit (NICU). Furthermore, activity monitoring using this method also has clinical significance including lethargy associated with over-sedation, hyperactivity related to under-sedation and/or neonatal pain, and deterioration en route to an advanced disease state such as sepsis. In an alternative implementation, such contextualization of physiological parameters may be used to improve the accuracy of a physiological parameter (including respiratory rate, heart rate, $SpO_2$, etc.) which may otherwise provide erroneous readings due to neonatal motion.

Figure 1:
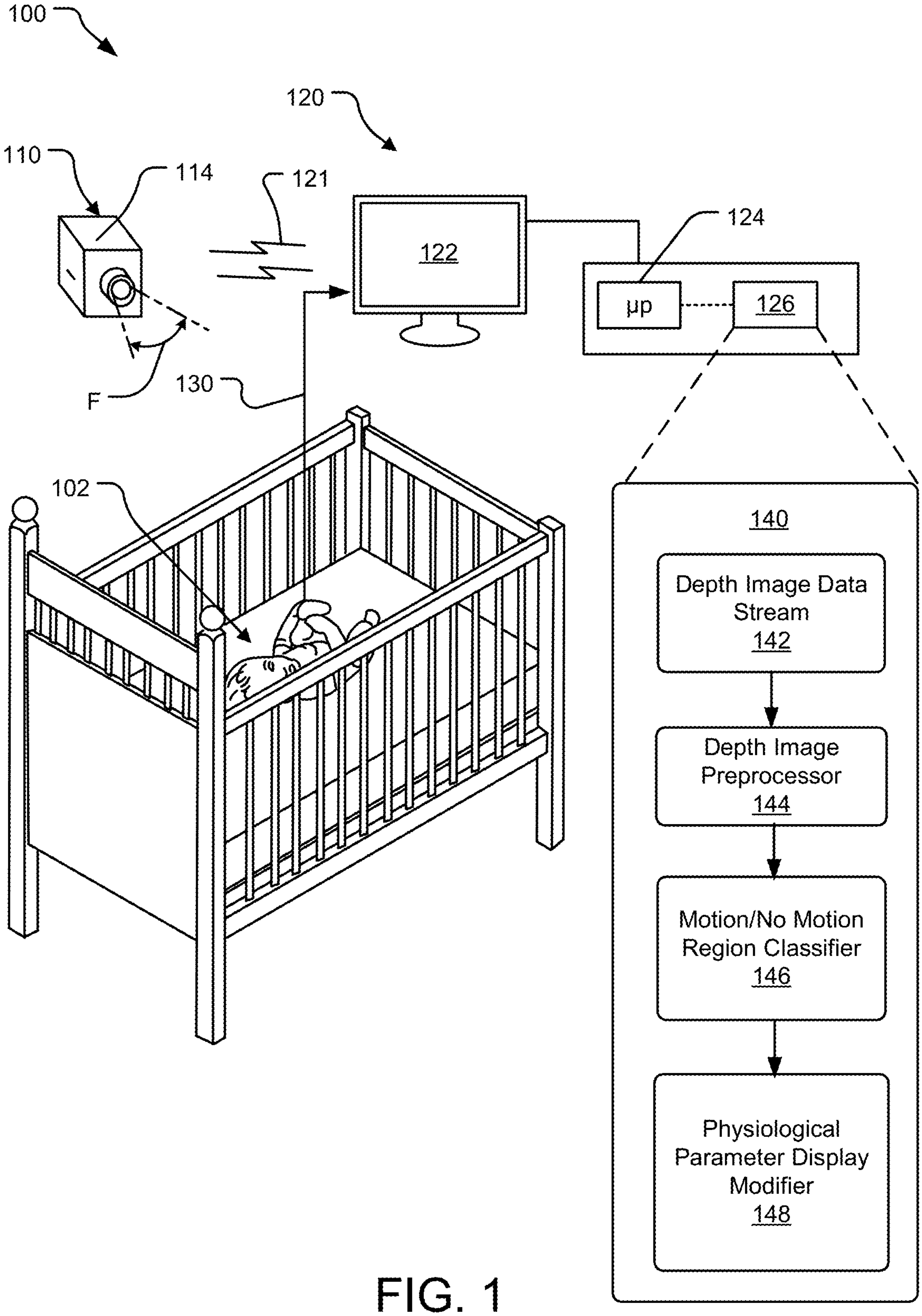

FIG. 1 illustrates a non-contact subject monitoring system 100 and a patient 102, in this particular example an infant in a crib. It is noted that the systems and methods described herein are not limited to a crib, but may be used with a bassinette, an incubator, an isolette, or any other place where the patient 102 is. The system 100 includes a non-contact detector system 110 placed remote from the patient 102. In this embodiment, the detector system 110 includes a camera system 114, particularly, a camera that includes an infrared (IR) detection feature. The camera system 114 may be a depth sensing camera system, such as a Kinect camera from Microsoft Corp. (Redmond, Washington) or a RealSense™ D415, D435 or D455 camera from Intel Corp. (Santa Clara, California).

The camera system 114 may operate at a set frame rate, which is the number of image frames taken per second (or other time period). Example frame rates include 20, 30, 40, 50, or 60 frames per second, greater than 60 frames per second, or other values between those. Frame rates of 20-30 frames per second produce useful signals, though frame rates above 100 or 120 frames per second may be helpful in avoiding aliasing with light flicker (for artificial lights having frequencies around 50 or 60 Hz).

The camera system 114 is remote from the patient 102, in that it is spaced apart from and does not physically contact the patient 102. The camera system 114 may be positioned in close proximity to or on the crib. The camera system 114 has a field of view F that encompasses at least a portion of the patient 102. The field of view F is selected to be at least the upper torso of the subject. However, as it is common for young children and infants to move within the confines of their crib, bed or other sleeping area, the entire area potentially occupied by the patient 102 (e.g., the crib) may be the field of view F.

The camera system 114 includes a depth sensing camera that can detect a distance between the camera system 114 and objects in its field of view F. Such information can be used to determine that the patient 102 is within the field of view of the camera system 114 and determine a region of interest (ROI) to monitor on the subject. The ROI may be the entire field of view F or may be less than the entire field of view F. Once an ROI is identified, the distance to the desired feature is determined and the desired measurement(s) can be made.

The measurements (e.g., one or more of depth signal, RGB reflection, light intensity) are sent to a computing device 120 through a wired or wireless connection 121. The computing device 120 includes a display 122, a processor 124, and hardware memory 126 for storing software and computer instructions. Sequential image frames of the patient 102 are recorded by the video camera system 114 and sent to the computing device 120 for analysis by the processor 124. The display 122 may be remote from the computing device 120, such as a video screen positioned separately from the processor and memory. Other embodiments of the computing device 120 may have different, fewer, or additional components than shown in FIG. 1. In some embodiments, the computing device may be a server. In other embodiments, the computing device of FIG. 1 may be connected to a server. The captured images (e.g., still images or video) can be processed or analyzed at the computing device and/or at the server to create a topographical map or image to identify the patient 102 and any other objects within the ROI.

Also in some embodiments, the computing device 120 is communicatively connected to a monitoring device (not shown) that collects a physiological signal 130 from the patient 102. For example, such physiological signal may be the patient oxygen rate from an oximeter, the patient heart rate from an electrocardiogram (ECG) monitor, the patient respiration rate, etc.

The memory 126 may be configured to store a physiological signal contextualization module 140 that stores various data and modules that may be used to monitor motion of the patient 102 and to ensure that the impact of the motion on measurement and display of the physiological signal 130 are mitigated. The physiological signal contextualization module 140 stores the data stream 142 of the depth images received from the detector system 110 and a depth image processor 144 processes the depth images to generate various machine learning (ML) input feature matrices. Such processing of the depth images to generate ML input feature matrix is described in further detail in one or more of the figures disclosed herein and further discussed below.

The ML input feature matrices are used to train a classifier 146. For example, the classifier 146 can be a machine learning algorithm that automatically orders or categorizes data in one or more classes. In one implementation, the classifier 146 may be used to classify whether a stream of depth image data stream represents a motion or not for the patient 102. Example implementation of the classifier 146 may be a perceptron classifier, a logistic regression classifier, a naïve bayes classifier, etc.

Subsequently the result of the classifier 146 may be input to a display modifier 148. For example, the display modifier 148 may modify a display of a physiological parameter about the patient 102. In one implementation, the display modifier 148 may modify display of a respiratory rate of the patient 102, an ECG chart of the patient 102, etc. For example, the display modifier 148 may superimpose the display of such physiological parameter with display of whether the patient 102, such as an infant, was in motion or not. For example, the part of the chart of the physiological parameter may be highlighted when the patient 102 is determined to be in motion. Alternatively, the color of the chart of the physiological parameter may be changed based on whether the patient 102 is in motion or not.

In an alternative implementation, the result of the classifier 146 may be used to generate a motion-flag that is added to the display of another physiological parameter such as display of the respiratory rate of the patient, an ECG chart of the patient, a PPG chart of the patient, etc. In one implementation, the result of the classifier 146 may be monitored to determine lack of motion by the patient for an extended period of time, such as more than a few minutes when the patient is awake or more than a few hours when the patient is asleep. Such extended lack of motion may indicate complications such as over-sedation, lethargy, etc. Subsequently, such detection of non-motion is used to generate a no-motion flag that may be added to the display of other physiological parameter such as display of the respiratory rate of the patient, an ECG chart of the patient, a PPG chart of the patient, etc.

Alternatively, the result of the classifier 146 may be used to generate a modifier signal that can be used to modify of filter the other physiological parameter such as display of the respiratory rate of the patient, an ECG chart of the patient, a PPG chart of the patient, etc. For example, a portion of the display of the ECG signal may be removed in the vicinity of the motion flag. In one implementation, such filtering or removal of a portion of the physiological signal may be only when the output of the classifier 146 suggests that the patient's motion is above a threshold. Yet alternatively, the result of the classifier 146 or the motion flag may be used to generate or modify an alarm signal. In one implementation, the result of the classifier 146 is provided to the display module that generates display of various physiological signals. Subsequently, the display module may incorporate the result of the classifier 146 to modify display of a physiological signal and/or an alarm signal based on such physiological signal.

Figure 2:
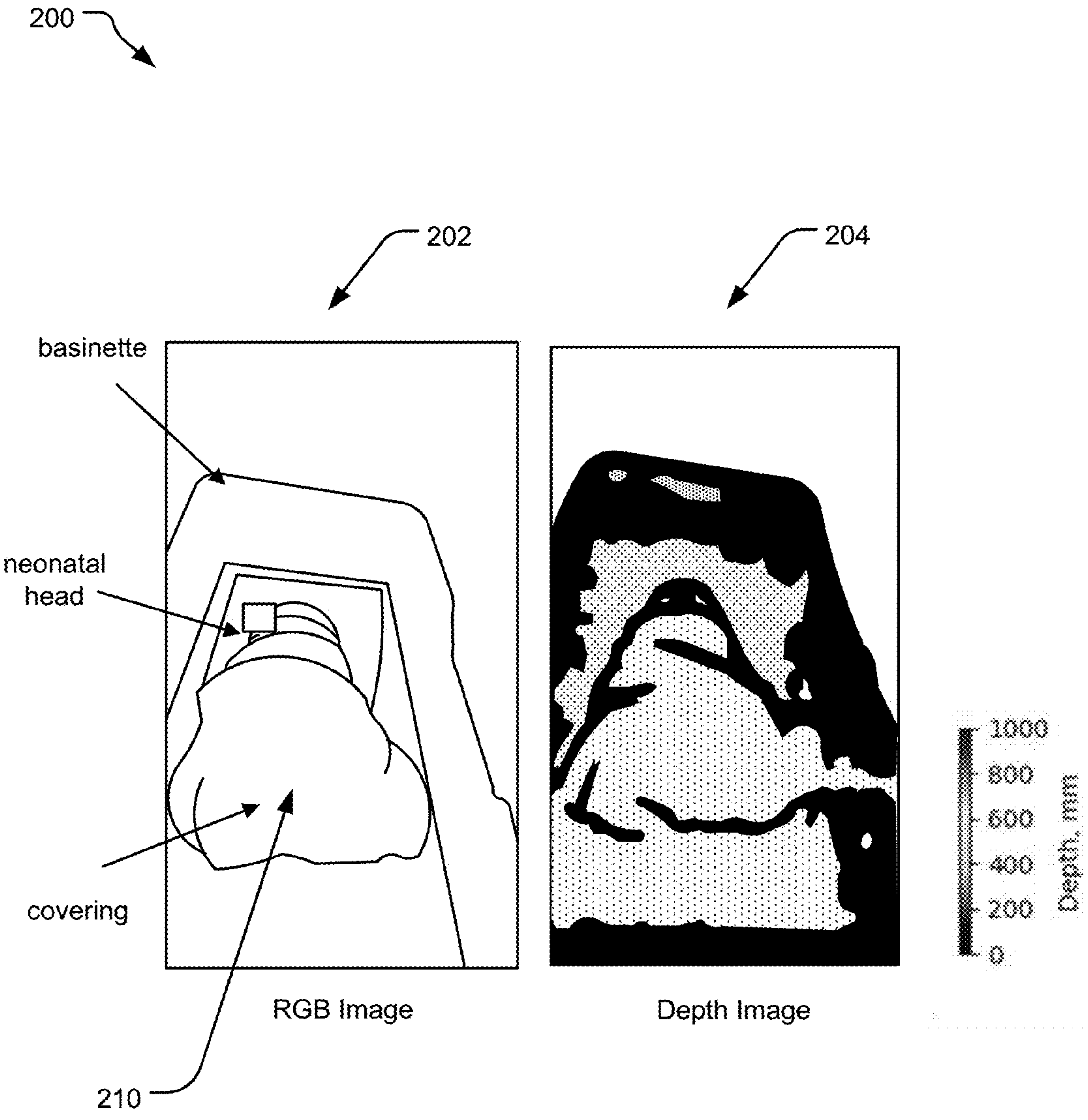

FIG. 2 indicates an example of a depth video image 200 of a neonatal patient. Specifically, a camera may generate an RGB image 202 and a corresponding depth image 204. The RGB image 202 indicates a neonatal patient 210 in a bassinette. The depth image 202 shows the depth of various components in the image, including the head of neonate, the bassinette at various depth levels in milli-meters (mm). The camera may generate a stream of the depth images 204 at predetermined intervals, such as at every second, every five seconds, etc., as selected by a user.

Figure 3A:
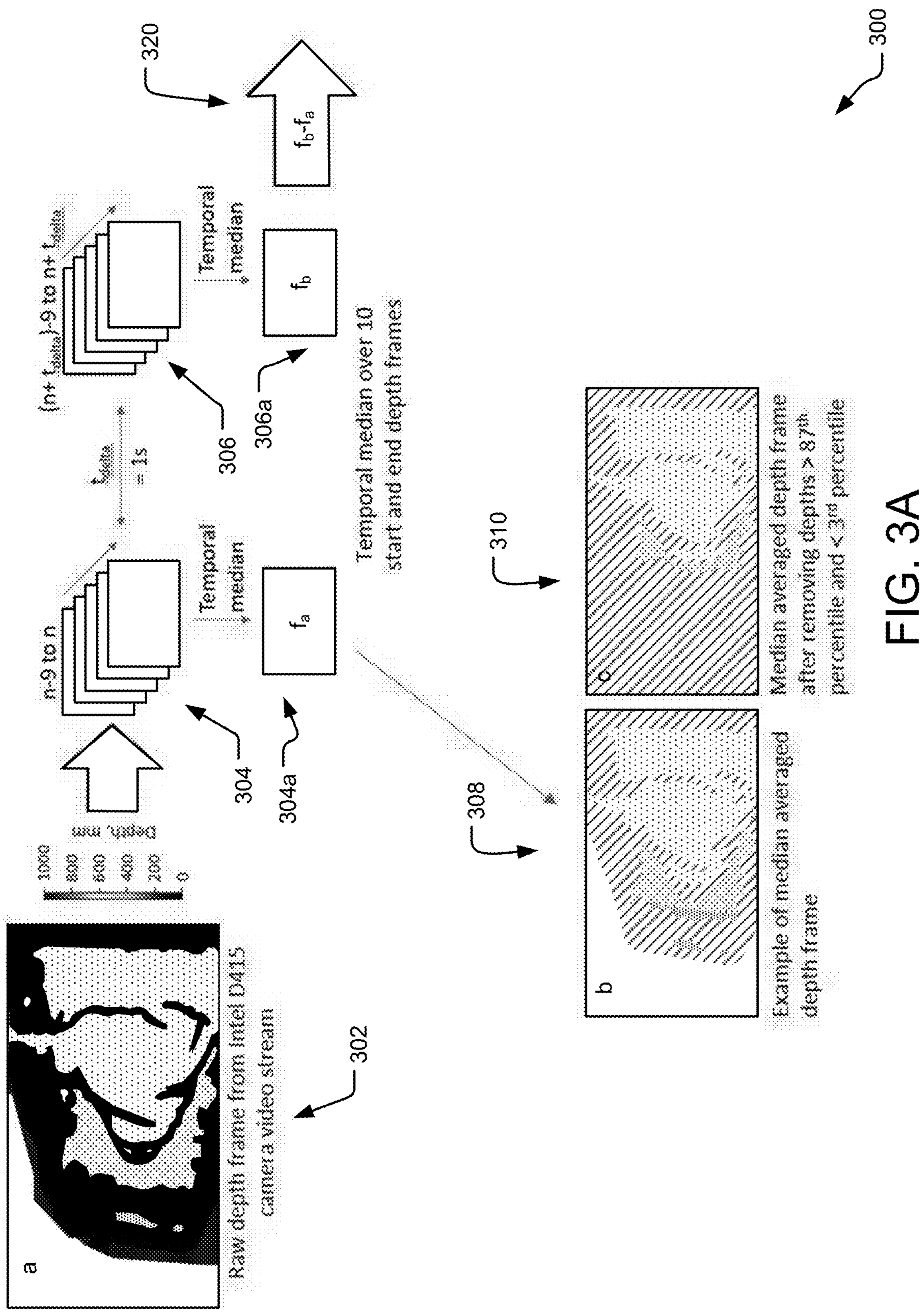
FIGS. 3A and 3B illustrates parts of the processing steps undertaken to denoise the depth image to generate a depth difference matrix.

FIG. 3A indicates parts of the processing steps 300 undertaken to denoise the depth image 302 to generate a depth difference matrix. The depth image 302 represents a raw depth image of a stream of depth images generated by a depth camera. For example, each pixel in the depth image 302 may represent a value indicating the depth of that pixel between 0 and 1000 mms. The stream of depth images is divided into set of images for a predetermined time span, such as for example one-second time span, with each timespan including a fixed number of depth frames. Subsequently, for each timespan, at a first point in time a first temporal median $f_a$ 304*a* average is computed over the first N frames 304 preceding the first point in time. Similarly, or each timespan, at a second point in time a second temporal median $f_b$ 306*a* is computed over the last N frames 306 preceding the second point in time. Here the second point in time is subsequent to the first point in time. The value of N may be provided as an input parameter by a user, in the illustrated example, N is 10.

An example, of a temporal median depth frame is shown by 308. In one implementation the median average depth frame 308 may be further processed to focus on the neonatal patient's location within the frame. For example, depths which are either too near or too far from the camera are removed based on user-specified percentile depth limits. For example, the depths greater than $87^{th}$ percentile and depths lower than $3^{rd}$ percentile are removed to get a modified depth median frame 310.

Figure 3B:
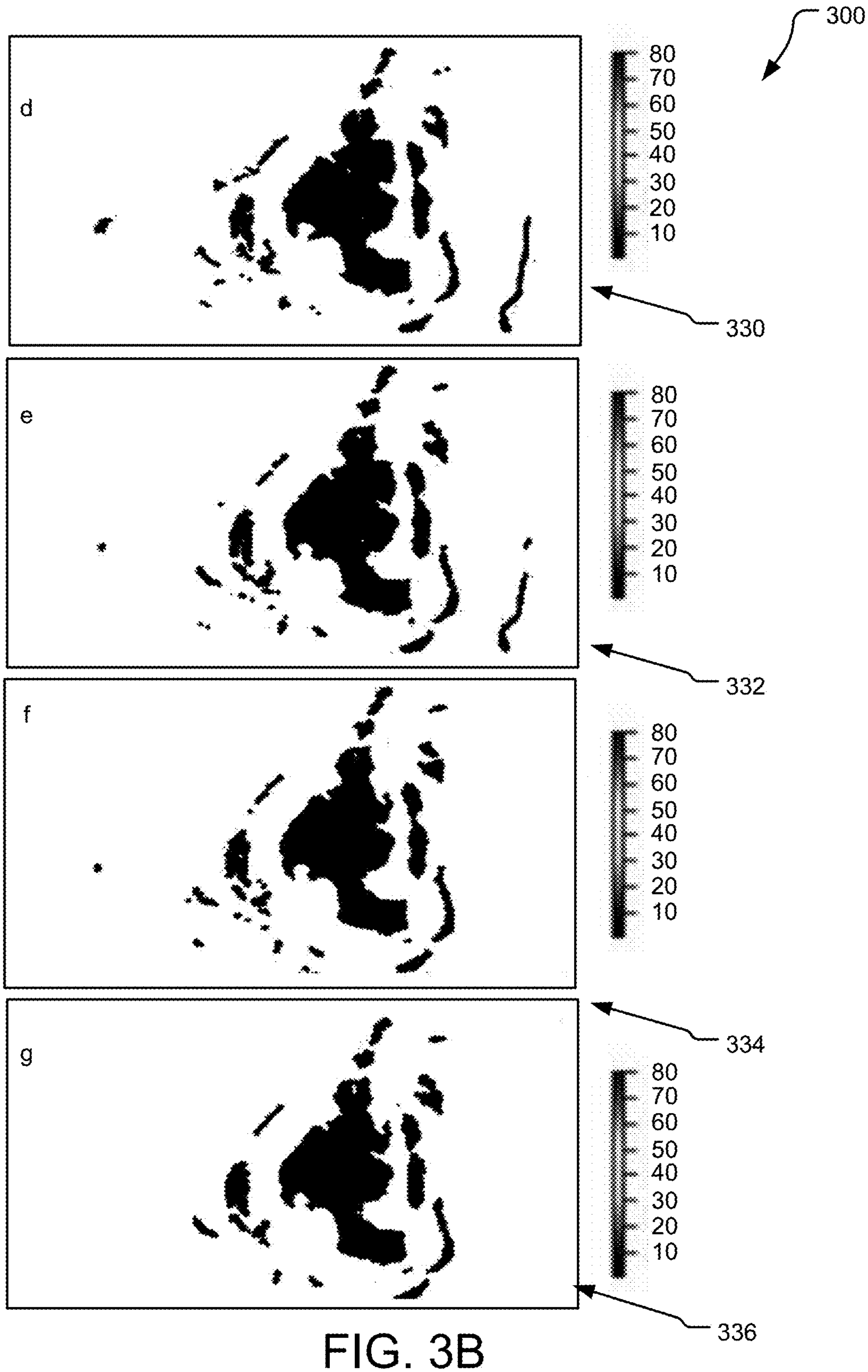

Subsequently, as shown by operation 320, the depth difference frames are computed by finding the difference between the two temporal median averaged depth frames $f_b$ 306*a* and $f_a$ 304*a* to generate a depth difference frame 330 as shown in FIG. 3B. The depth difference frame 330 may be further denoised by applying spatial median filtering, such as 5×5 or 3×3 spatial median filtering to get the denoised depth difference frame 332. Applying such median filter of kernel size 5×5 removes small regions of unusually high depth differences by applying a moving 5×5 window over the frame and returning the median depth difference of all pixels within the window.

Alternatively, depth differences that do not correspond to neonatal motion, such as too large depth differences such as over 150 mm, are removed to generate alternate denoised depth difference frame 334. In another implementation, area-based connected component removal is applied to identify and remove small pixel regions (connected areas of under 40 pixels) containing valid depth differences, as they are considered too small to be gross movements of the baby, to generate an alternate denoised depth difference frame 336.

In alternative implementations, one or more of the denoising processes to generate the alternate denoised depth difference frames 334-336 are selectively applied. For example, depth differences higher than a threshold depth difference may be filtered out. Subsequently, the denoised depth difference frame can be used to derive input features over time where such input features are indicative of the amount of movement by the patient over various ranges and scales.

Figure 4:
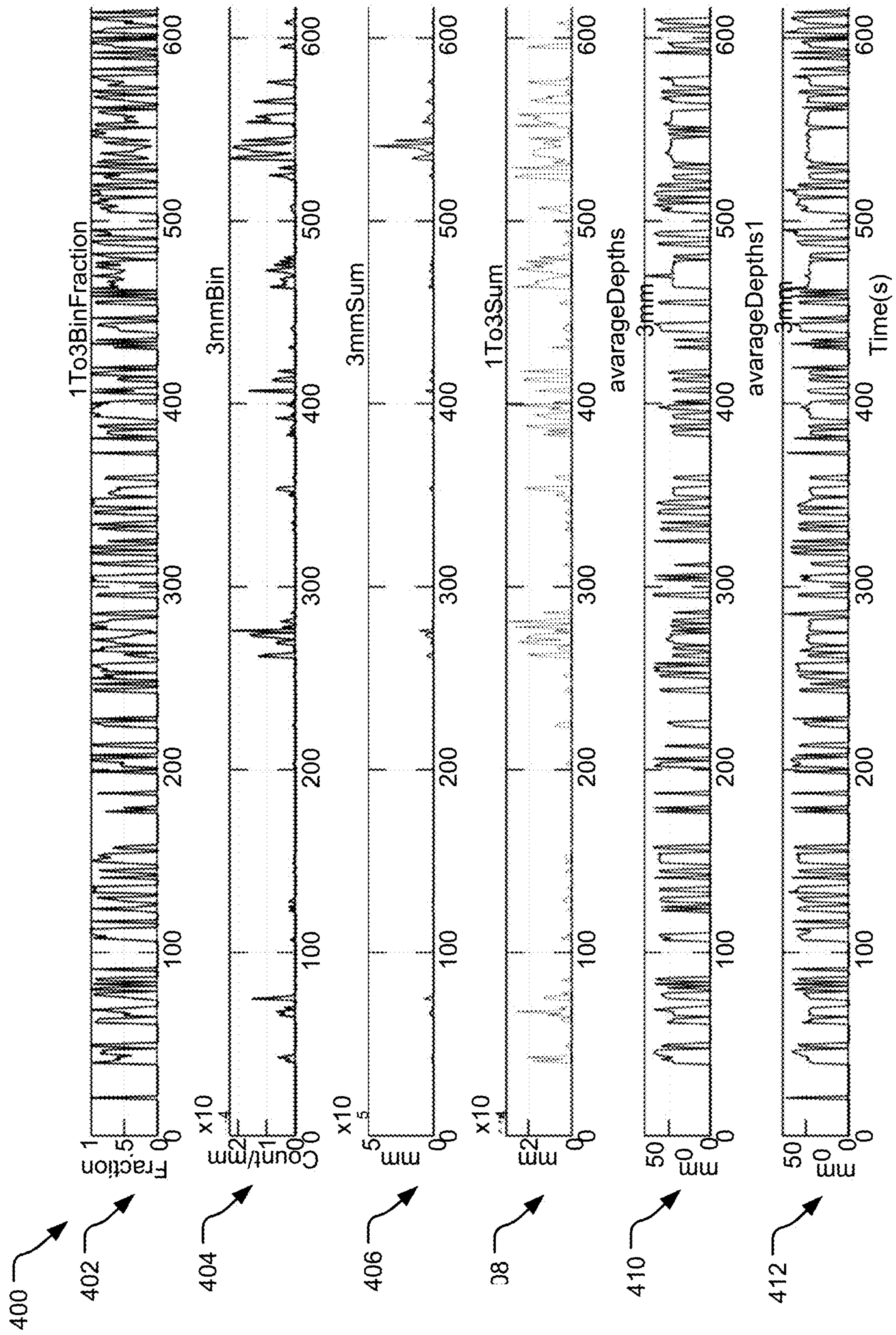
FIG. 4 illustrates various example input features.

One or more such input features are disclosed in further detail in FIG. 4. The features disclosed herein may be used as an input feature for a machine learning algorithm to train the machine to classify a series of depth frames in different classes. For example, such classifier may classify the series of frames as representing a motion or not representing a motion. For example, 402 and 404 represent the spatial scale of motion and enable the model to detect smaller motions over a larger spatial area. Specifically, 402 represents fraction of all non-null pixels where the depth difference in in the range of 1-3 mm, whereas 404 represents number of pixels with depth difference above 3 mm.

Similarly, the summed depth difference features 406 and 408 represent the magnitude of motion, allowing detection of larger motions over smaller spatial areas. Specifically, 406 represents a sum of depth differences for pixels where depth differences are greater than 3 mm, whereas 408 represents sum of depth differences for pixels where the depth difference is in the range of 1-3 mm.

The features 410 and 412 are averaged depth features that are intended to represent depth difference features with respect to distance from the camera, such that the machine learning model is able to learn motions of different scale and magnitude regardless of where the camera is placed. Specifically, 410 represents mean depth of all pixels where the depth difference is greater than 3 mm, whereas 412 represents mean depth of all pixels where depth difference is in the range of 1-3 mm.

In alternative implementations, other features may be derived from the depth video streams indicating other depth/depth difference ranges and/or measures indicative of motion variability. For example, to further represent motion variability, measures such as the mean or median of per-pixel standard deviation of depths within the frame can be included as additional features. In addition, denoising parameters described above, including the number of temporally averaged depth frames, percentile depth limits, spatial median filter kernel size and connected component area limits, can be specified as input parameters to the ML model. Additionally, the depth difference ranges used to extract depth/depth difference-based features can be altered to represent varying spatial scales and magnitudes of motion and can be included as additional features.

Any of the features disclosed above may be used as input features for machine learning models. For example, one of the input features may be used to train a decision tree classifier or random forest classifier to classify periods of motion. Alternatively other classifiers may also be used in the method including, but not limited to: Support Vector Machine, kNN, AdaBoost, Boosted Trees, Linear Regression, Naïve Bayes or a Neural Network classifier.

Figure 5:
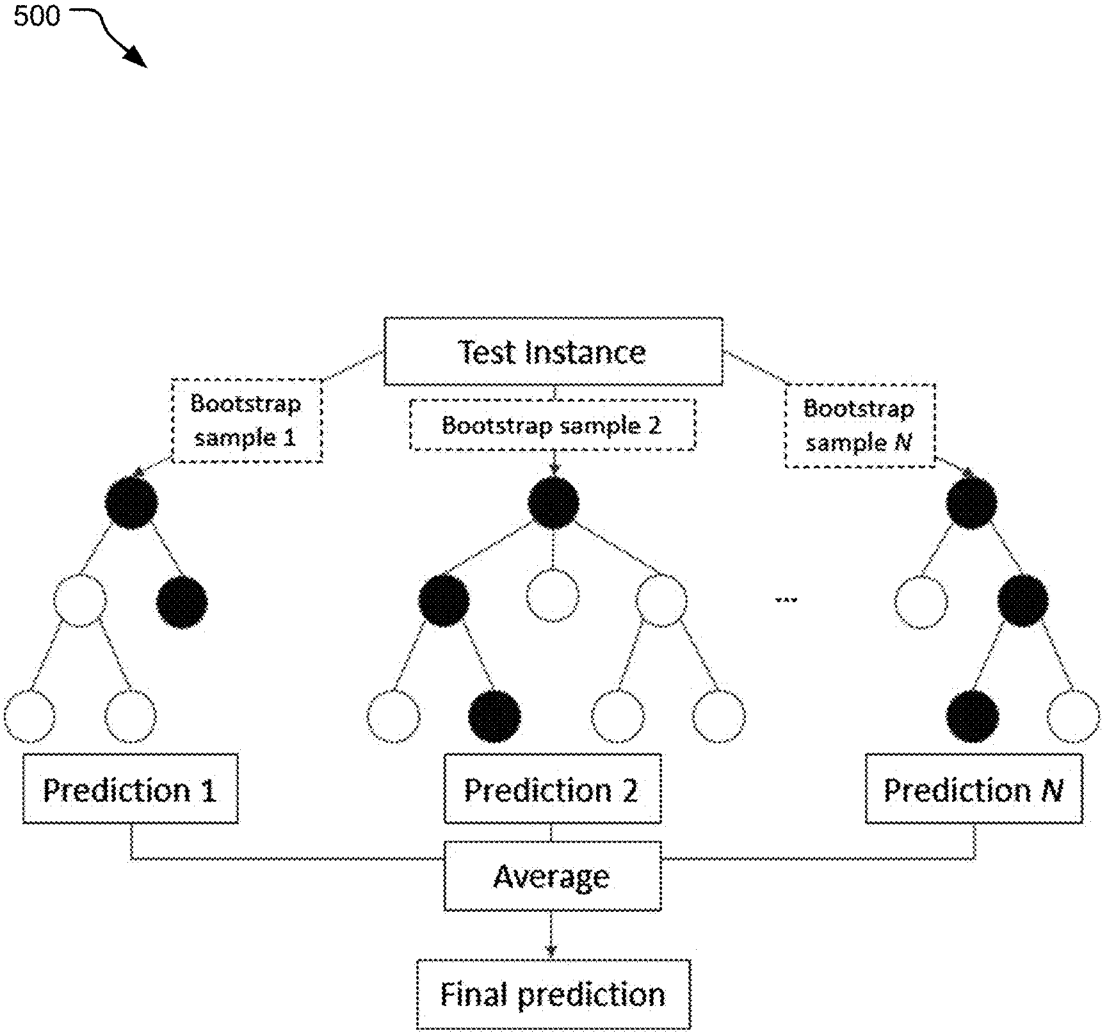
FIG. 5 illustrates example schematic of a random forest classifier.

FIG. 5 illustrates example schematic 500 of a random forest classifier. The classifier may be trained on labeled data of neonate's motion (derived from manual observation of the RGB video data set) and then tested on unseen validation data. The classifier in this example was trained and tested on the neonatal data set using a leave-one-out cross validation (LOOCV) approach.

Figure 6:
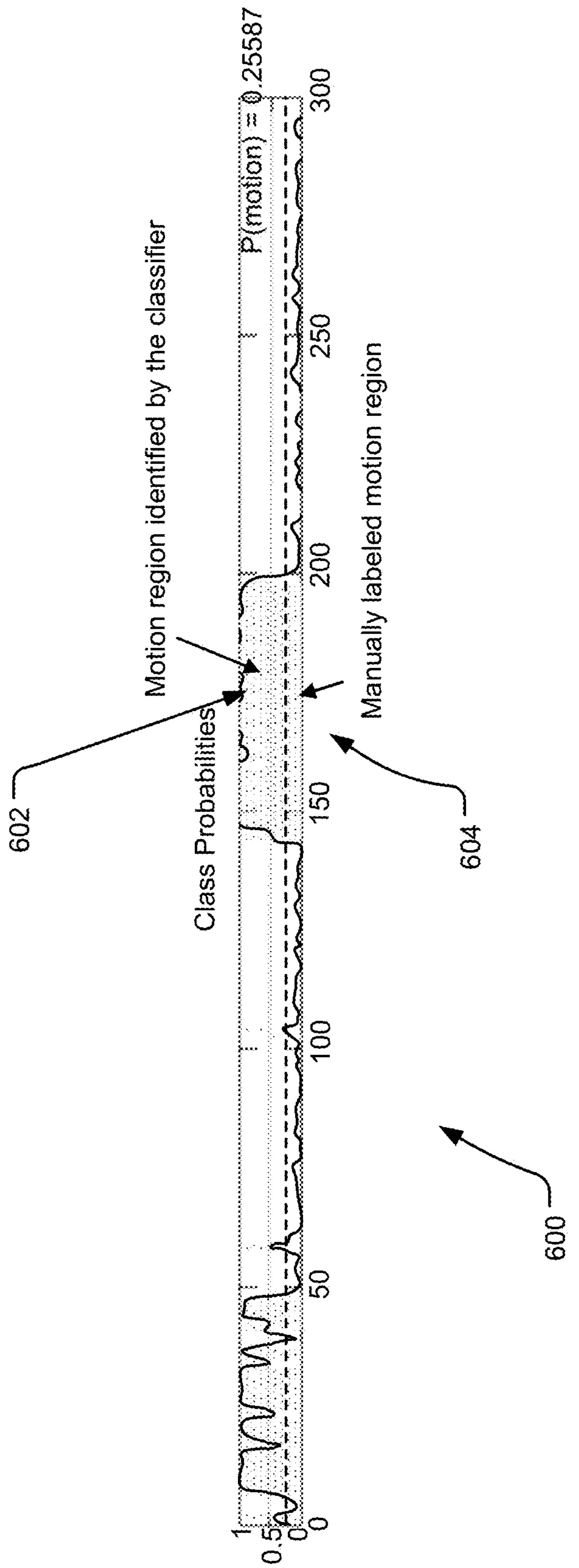
FIG. 6 illustrates an example feature labeled with detected motion as identified by the classifier and manually detected motion.

FIG. 6 illustrates an example output class probability signal 600 labeled with detected motion 602 as identified by the classifier and manually detected motion 604. As illustrated here, the detected motion 602 as identified by the classifier generally corresponds with the manually detected motion 604.

Figure 7:
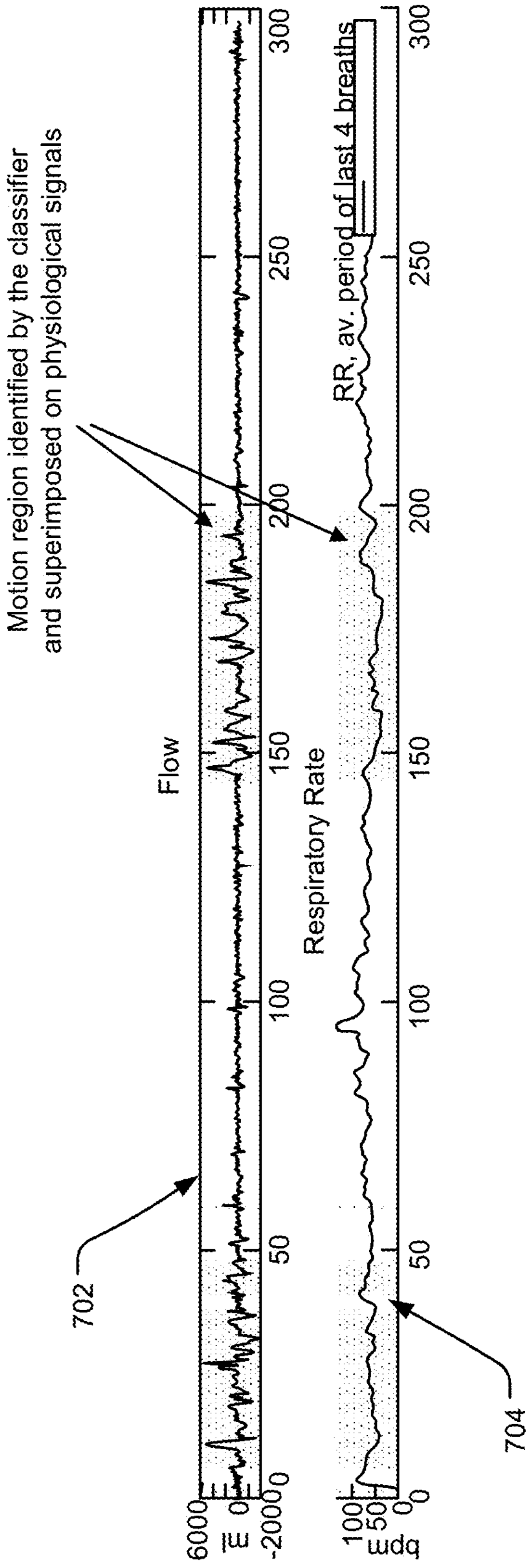
FIG. 7 illustrates modifying display of physiological signal or parameter of the patient with information about motion of the patient.

FIG. 7 illustrates modifying display of physiological signal or parameter of the neonate with information about motion of the neonate. For example, 702 indicates motion superimposed on a flow signal and 704 indicates motion superimposed on a respiratory rate signal.

Figure 8:
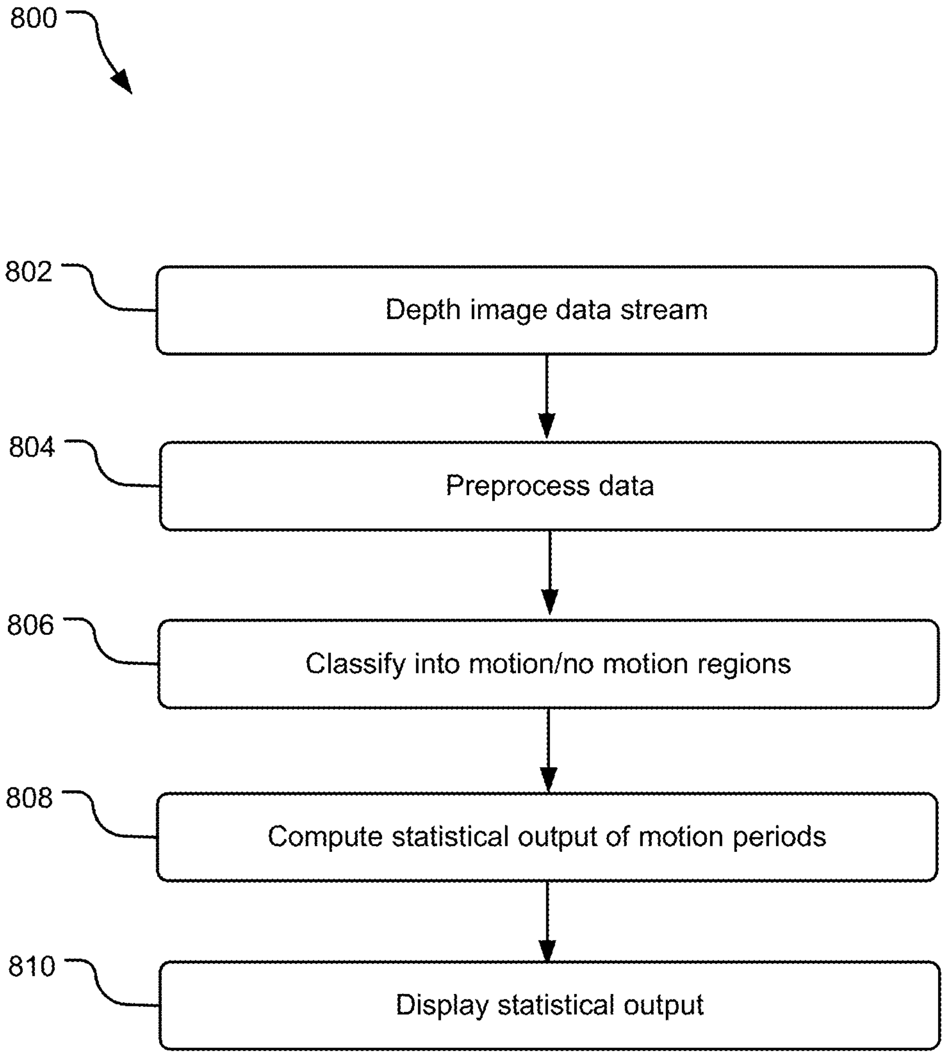
FIG. 8 illustrates operations for using the output of the motion detector classifier to determine neonatal activity.

FIG. 8 illustrates operations 800 for using the output of the motion detector classifier to determine neonatal activity such as the number of movement episodes, characteristics of the duration of movement (e.g., total duration, average duration of a movement episode, longest period, standard deviation, the percent of time movement took place, etc.). A clinician may use these output statistics to determine how lethargic a baby is and to determine what therapeutic intervention may be necessary.

Specifically, an operation 802 generates a depth image data stream that is preprocessed at operation 804 to generate input features in the manner described above. An operation 806 classifies a stream of depth images to classify them in motion and no-motion regions. Subsequently, an operation 808 generates various statistics, which are displayed at an operation 810. The statistical output may be displayed on the screen, or it may be recorded for future use. Alternatively, it may be computed over various periods of time including the whole stay of the neonate, every day, every 8 hours, every 4 hours, 2 hours, 1 hour, 30 minutes etc. In one implementation, the statistics may be updated as a rolling window over these periods and sent to a patient record system.

In yet another implementation, the motion detection classifier may also be used to improve determination of physiological signals. For example, a respiration rate algorithm may calculate the respiration rate as the average of a number of recently detected breaths. With the addition of the motion classification signal, the algorithm may "downweight" any breaths that are found during motion—leading to the calculation of a more robust respiration rate. In an alternative implementation, the respiration rate algorithm may hold its value for longer during a period of motion. Note that this could be done for many algorithms (e.g. for heart rate, $SpO_2$, blood pressure, temperature, etc.) and for many devices, with respiration rate from a depth camera system being just an example.

Figure 9:
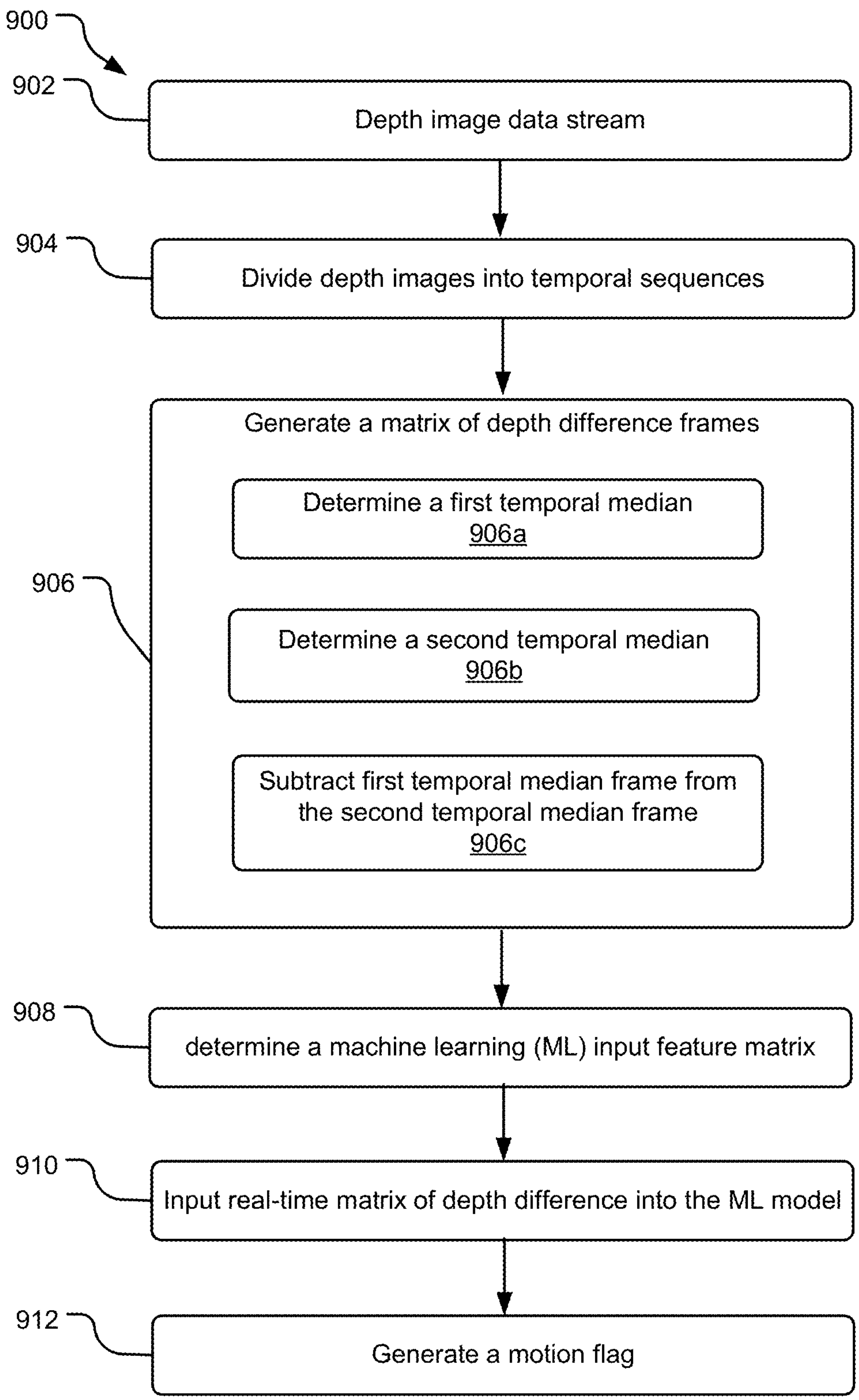
FIG. 9 illustrates alternative operations for generating an input feature matrix for training a motion detection classifier.

FIG. 9 illustrates alternative operations 900 for generating an input feature matrix for training a motion detection classifier or to use a trained classifier to classify series of depth images into motion or no-motion classes. Specifically, an operation 902 receives a stream of depth images. An operation 904 divides the depth images into a number of temporal video sequences, each of the temporal video sequences having N frames each being $t_{delta}$ apart from each other. For example, $t_{delta}$ may be one second. An operation 906 generates a matrix of depth difference frames. For example, generating the depth difference frames includes an operation 906*a* that at time $t=t_a$, determines a first temporal median $f_a$ of previous N depth frames, where N may be 5, 10, 15, frames etc. Subsequently, an operation 906*b*, at time $t_b=t_a+t_{delta}$, determines a second temporal median $f_b$ of previous N depth frames.

An operation 906*c* generates the depth difference frame by subtracting the first temporal median $f_a$ from the second temporal median $f_b$. An operation 908 determines a machine learning (ML) input feature matrix. The ML input feature matrix may be used to train an ML model such as a motion detection classifier. Subsequently, at operation 910, real-time matrix of depth difference frames may be input into the trained ML model to identify an area of motion by the patient. An operation 912 may generate a motion flag based on the identified area of motion by the patient. Furthermore, the identified area of motion or the motion flag may be super-imposed on a time-series display of a physiological signal of the patient. For example, the identified area of motion or the motion flag may be super-imposed on a display of an ECG signal of the patient.

Figure 10:
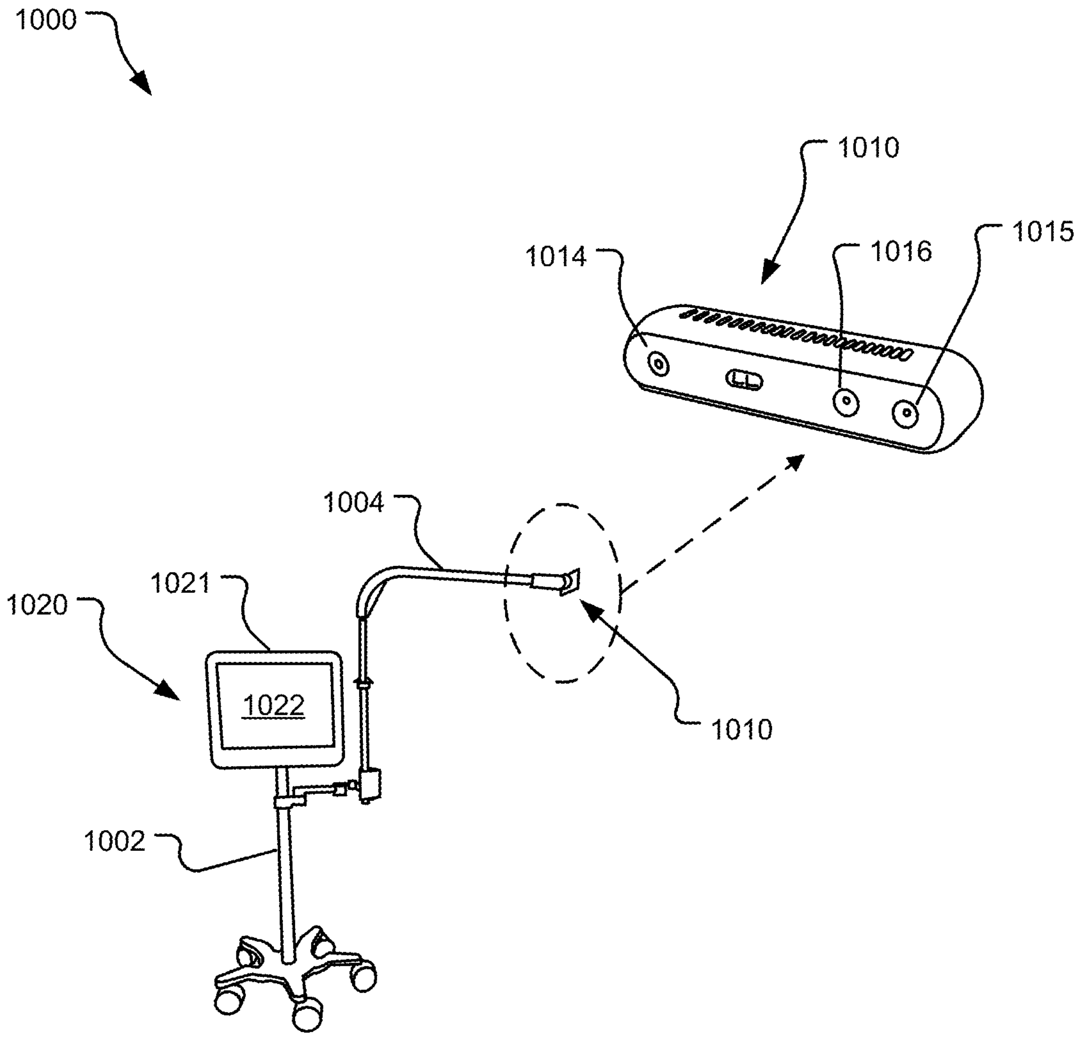
FIG. 10 shows a portable non-contact subject monitoring system that includes a non-contact detector and a computing device.

FIG. 10 shows a portable non-contact subject monitoring system 1000 that includes a non-contact detector 1010 and a computing device 1020. In this embodiment, the non-contact detector 1010 and the computing device 1020 are generally fixed in relation to each other and the system 1000 is readily moveable in relation to the subject to be monitored. The detector 1010 and the computing device 1020 are supported on a trolley or stand 1002, with the detector 1010 on an arm 1004 that is pivotable in relation to the stand 1002 as well as adjustable in height. The system 1000 can be readily moved and positioned where desired.

The detector 1010 includes a first camera 1014 and a second camera 1015, at least one of which includes an infrared (IR) camera feature. The detector 1010 also includes an IR projector 1016, which projects individual features (e.g., dots, crosses or Xs, lines, or a featureless pattern, or a combination thereof etc.).

The detector 1010 may be wired or wireless connected to the computing device 1020. The computing device 1020 includes a housing 1021 with a touch screen display 1022, a processor (not seen), and hardware memory (not seen) for storing software and computer instructions.

Figure 11:
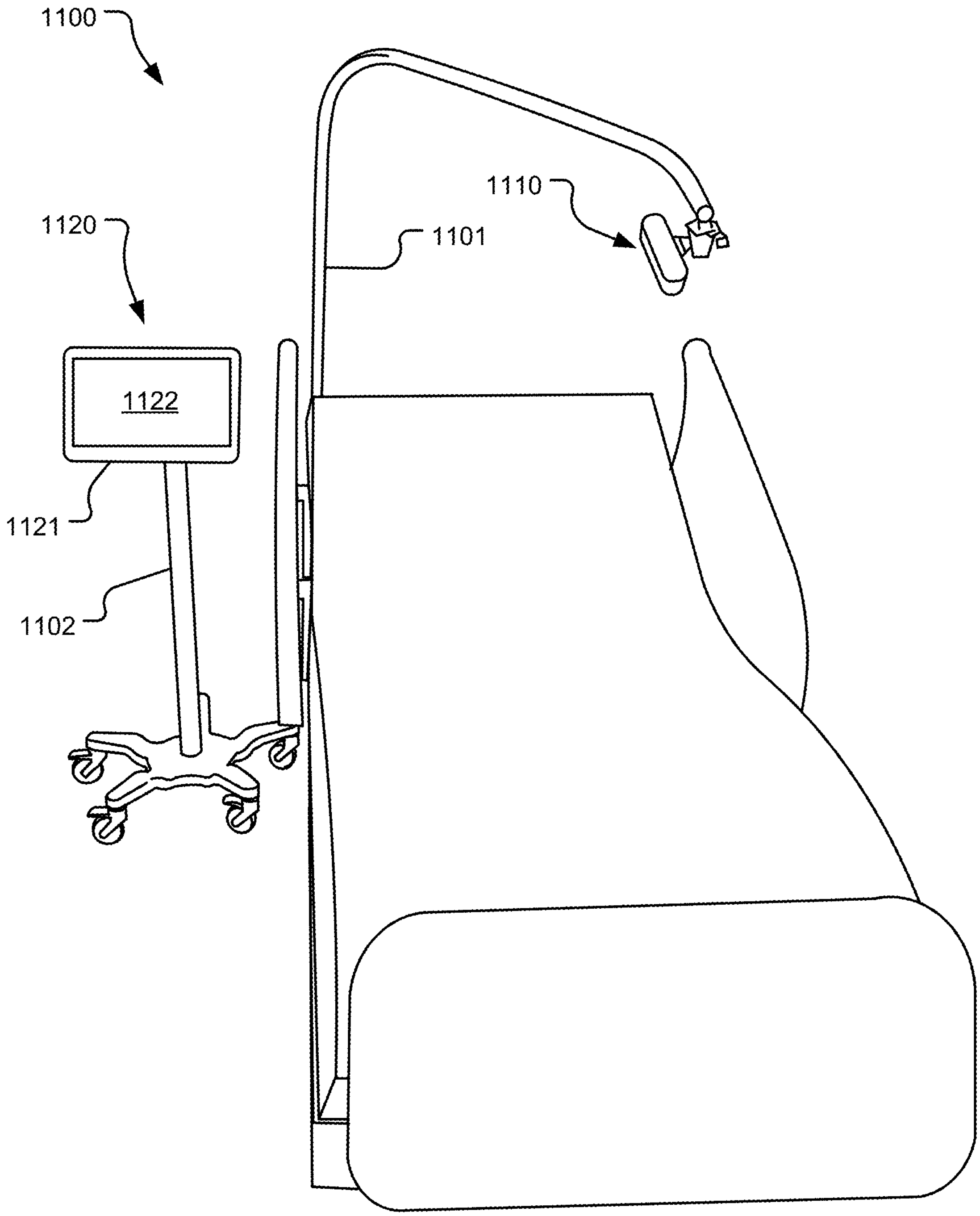
FIG. 11 shows a semi-portable non-contact subject monitoring system that includes a non-contact detector and a computing device.

FIG. 11 shows a semi-portable non-contact subject monitoring system 1100 that includes a non-contact detector 1110 and a computing device 1120. In this embodiment, the non-contact detector 1110 is in a fixed relation to the subject to be monitored and the computing device 1120 is readily moveable in relation to the subject.

The detector 1110 is supported on an arm 1101 that is attached to a bed, in this embodiment, a hospital bed, although the detector 1110 and the arm 1101 can be attached to a crib, a bassinette, an incubator, an isolette, or other bed-type structure. In some embodiments, the arm 1101 is pivotable in relation to the bed as well as adjustable in height to provide for proper positioning of the detector 1110 in relation to the subject.

The detector 1110 may be wired or wireless connected to the computing device 1120, which is supported on a moveable trolley or stand 1102. The computing device 1120 includes a housing 1121 with a touch screen display 1122, a processor (not seen), and hardware memory (not seen) for storing software and computer instructions.

Figure 12:
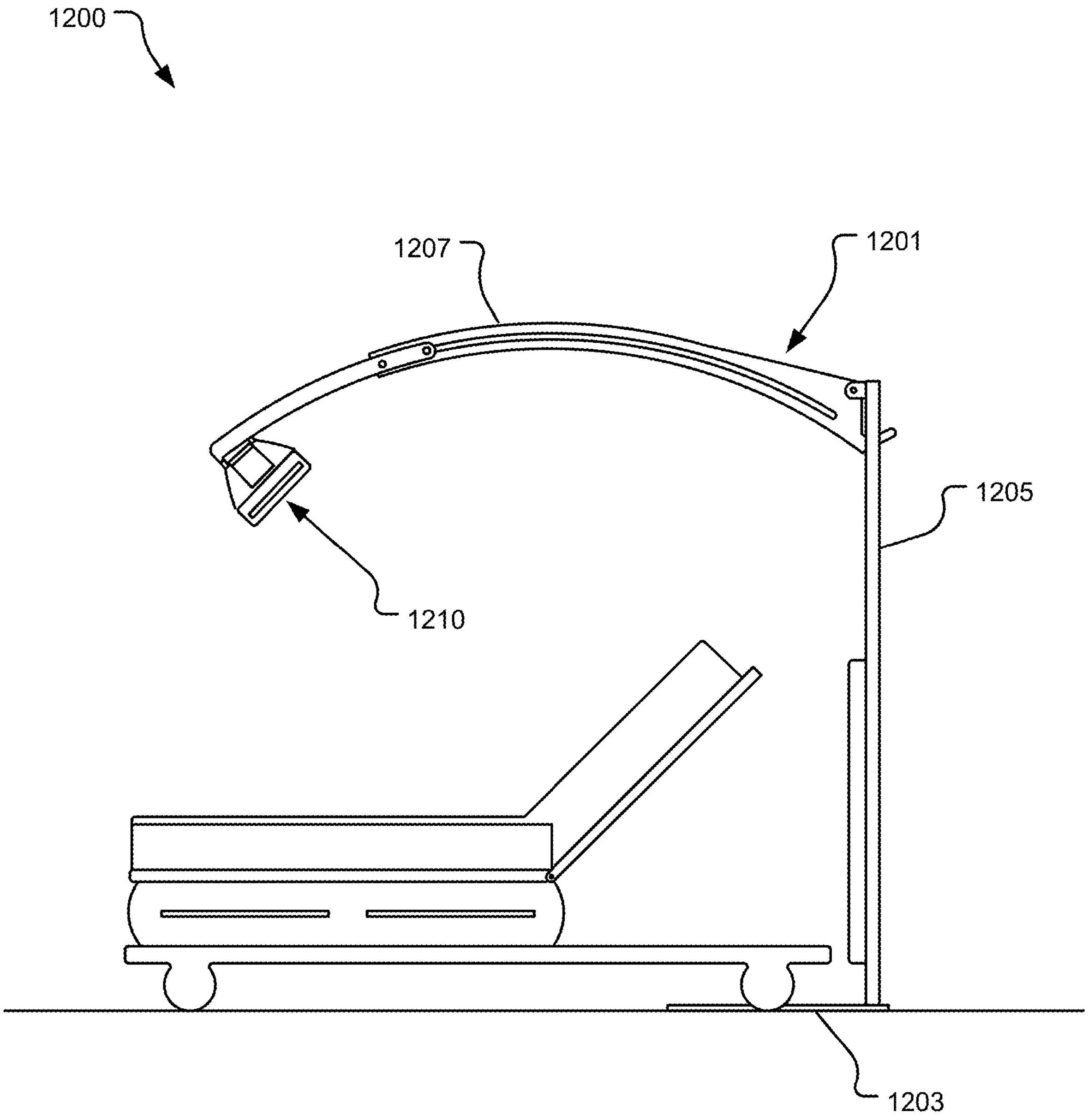
FIG. 12 shows a non-portable non-contact subject monitoring system that includes a non-contact detector and a computing device.

FIG. 12 shows a non-portable non-contact subject monitoring system 1200 that includes a non-contact detector 1210 and a computing device (not seen in FIG. 12). In this embodiment, at least the non-contact detector 1210 is generally fixed in a location, configured to have the subject to be monitored moved into the appropriate position to be monitored.

The detector 1210 is supported on a stand 1201 that is free standing, the stand having a base 1203, a frame 1205, and a gantry 1207. The gantry 1207 may have an adjustable height, e.g., movable vertically along the frame 1205, and may be pivotable, extendible and/or retractable in relation to the frame 1205. The stand 1201 is shaped and sized to allow a bed or bed-type structure to be moved (e.g., rolled) under the detector 1210.

Figure 13:
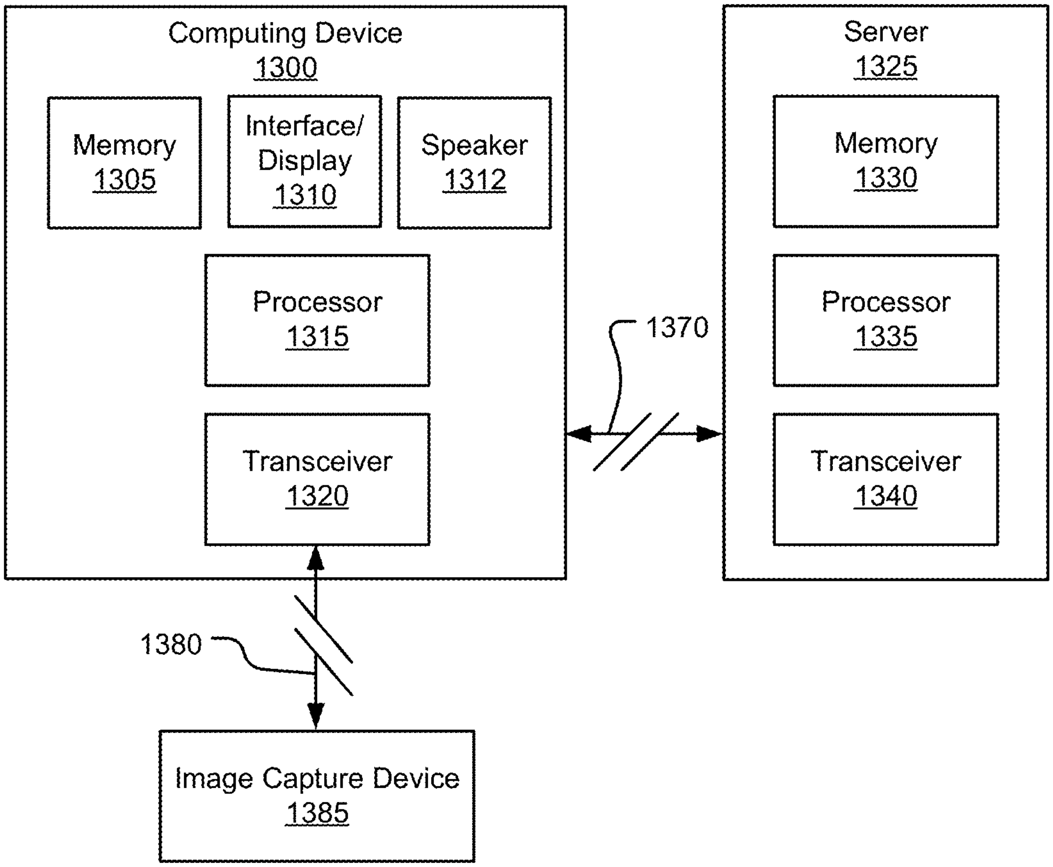
FIG. 13 is a block diagram illustrating a system including a computing device, a server, and an image capture device.

FIG. 13 is a block diagram illustrating a system including a computing device 1300, a server 1325, and an image capture device 1385 (e.g., a camera, e.g., the camera system 114 or cameras 214, 215). In various embodiments, fewer, additional and/or different components may be used in the system.

The computing device 1300 includes a processor 1315 that is coupled to a memory 1305. The processor 1315 can store and recall data and applications in the memory 1305, including applications that process information and send commands/signals according to any of the methods disclosed herein. The processor 1315 may also display objects, applications, data, etc. on an interface/display 1310 and/or provide an audible alert via a speaker 1312. The processor 1315 may also or alternately receive inputs through the interface/display 1310. The processor 1315 is also coupled to a transceiver 1320. With this configuration, the processor 1315, and subsequently the computing device 1300, can communicate with other devices, such as the server 1325 through a connection 1370 and the image capture device 1385 through a connection 1380. For example, the computing device 1300 may send to the server 1325 information determined about a subject from images captured by the image capture device 1385, such as depth information of a subject or object in an image.

The server 1325 also includes a processor 1335 that is coupled to a memory 1330 and to a transceiver 1340. The processor 1335 can store and recall data and applications in the memory 1330. With this configuration, the processor 1335, and subsequently the server 1325, can communicate with other devices, such as the computing device 1300 through the connection 1370.

The computing device 1300 may be, e.g., the computing device 120 of FIG. 1 or the computing device 220 of FIG. 2. Accordingly, the computing device 1300 may be located remotely from the image capture device 1385, or it may be local and close to the image capture device 1385 (e.g., in the same room). The processor 1315 of the computing device 1300 may perform any or all of the various steps disclosed herein. In other embodiments, the steps may be performed on a processor 1335 of the server 1325. In some embodiments, the various steps and methods disclosed herein may be performed by both of the processors 1315 and 1335. In some embodiments, certain steps may be performed by the processor 1315 while others are performed by the processor 1335. In some embodiments, information determined by the processor 1315 may be sent to the server 1325 for storage and/or further processing.

The devices shown in the illustrative embodiment may be utilized in various ways. For example, either or both of the connections 1370, 1380 may be varied. For example, either or both the connections 1370, 1380 may be a hard-wired connection. A hard-wired connection may involve connecting the devices through a USB (universal serial bus) port, serial port, parallel port, or other type of wired connection to facilitate the transfer of data and information between a processor of a device and a second processor of a second device. In another example, one or both of the connections 1370, 1380 may be a dock where one device may plug into another device. As another example, one or both of the connections 1370, 1380 may be a wireless connection. These connections may be any sort of wireless connection, including, but not limited to, Bluetooth connectivity, Wi-Fi connectivity, infrared, visible light, radio frequency (RF) signals, or other wireless protocols/methods. For example, other possible modes of wireless communication may include near-field communications, such as passive radio-frequency identification (RFID) and active RFID technologies. RFID and similar near-field communications may allow the various devices to communicate in short range when they are placed proximate to one another. In yet another example, the various devices may connect through an internet (or other network) connection. That is, one or both of the connections 1370, 1380 may represent several different computing devices and network components that allow the various devices to communicate through the internet, either through a hard-wired or wireless connection. One or both of the connections 1070, 1080 may also be a combination of several modes of connection.

The configuration of the devices in FIG. 13 is merely one physical system on which the disclosed embodiments may be executed. Other configurations of the devices shown may exist to practice the disclosed embodiments. Further, configurations of additional or fewer devices than the ones shown in FIG. 13 may exist to practice the disclosed embodiments. Additionally, the devices shown in FIG. 13 may be combined to allow for fewer devices than shown or separated such that more than the three devices exist in a system. It will be appreciated that many various combinations of computing devices may execute the methods and systems disclosed herein. Examples of such computing devices may include other types of infrared cameras/detectors, night vision cameras/detectors, other types of cameras, radio frequency transmitters/receivers, smart phones, personal computers, servers, laptop computers, tablets, RFID enabled devices, or any combinations of such devices.

In contrast to tangible or non-transitory computer-readable storage media, intangible or transitory computer-readable communication signals may embody computer-executable instructions, data structures, program modules or other data resident in a modulated data signal, such as a carrier wave or other signal transport mechanism. In one implementation, the tangible or non-transitory computer-readable storage media may be implemented as a physical article of manufacture including one or more tangible computer readable storage media. The term "modulated data signal" means a signal that has one or more of its characteristics set or changed in such a manner as to encode information in the signal. By way of example, and not limitation, intangible communication signals include wired media such as a wired network or direct-wired connection, and wireless media such as acoustic, RF, infrared and other wireless media.

Figure 14:
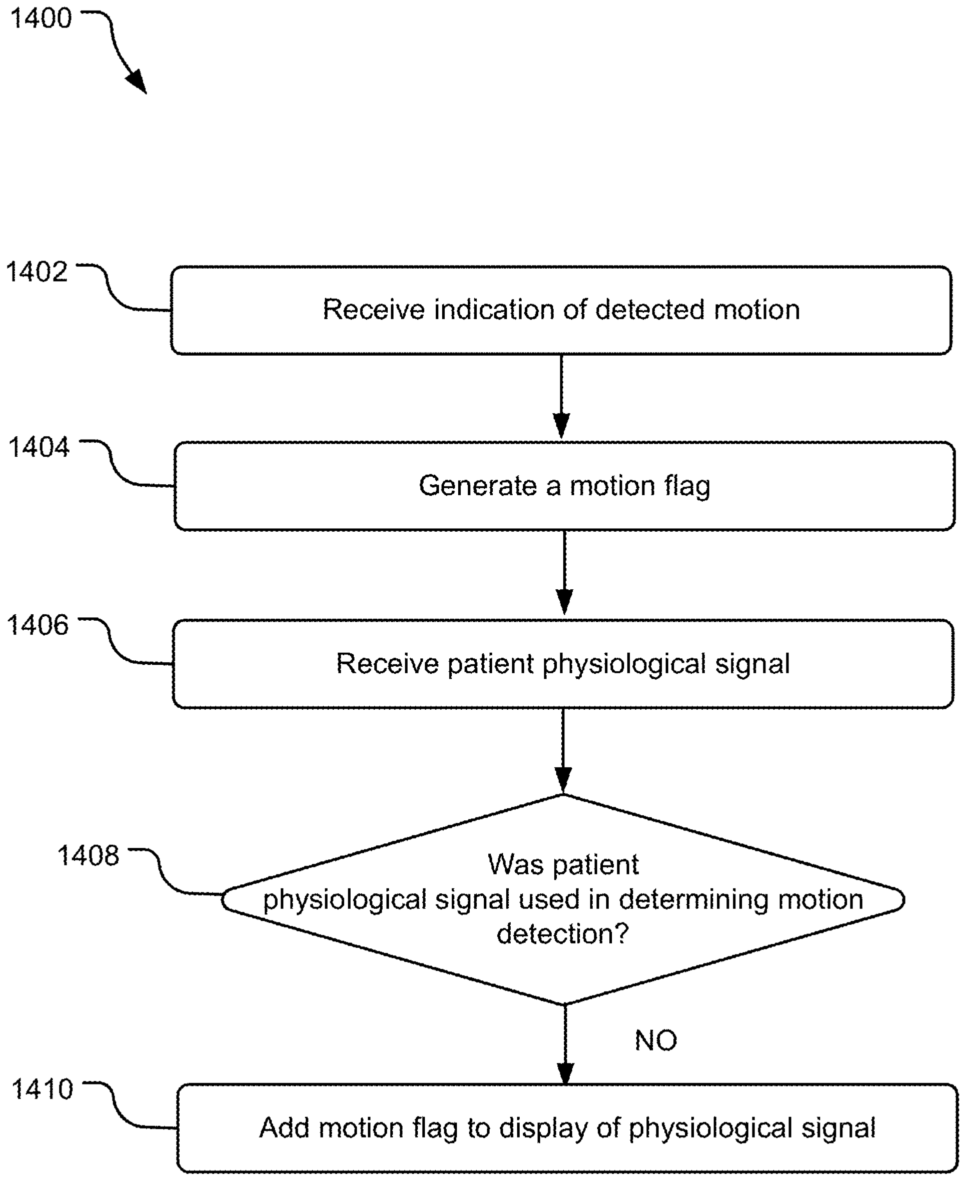
FIG. 14 illustrates example operations for displaying a motion flag on a display of a physiological signal of the patient based on the motion of the patient as determined by the system disclosed herein.

FIG. 14 illustrates operations 1400 for displaying a motion flag on a display of a physiological signal of the patient based on the motion of the patient as determined by the system disclosed herein. Specifically, the operations 1400 may generate and display a motion flag on the display of a physiological signal of the patient. For example, such physiological signal may be a breathing flow signal, an electrocardiogram (ECG) signal, a photoplethysmography (PPG) signal, etc.

Specifically, an operation 1402 receives an indication of the detected motion of the patient. For example, such an indication of the detected motion may be generated by a classifier such as the classifier 146 disclosed in FIG. 1. An operation 1404 generates a motion flag based on the indicator or the detected motion. An operation 1406 receives a physiological signal of the patient, such as an ECG signal, a PPG signal, etc. Subsequently, an operation 1410 may add the motion flag to the display of a physiological signal, such as the ECG signal. Alternatively, the operation 1410 may merely send the motion flag to a device that displays the ECG signal. Subsequently, the display device may display the motion flag on the display of the ECG signal. Similarly, in case of the physiological signal being the PPG signal, operation 1410 adds the motion flag to the display of the PPG signal. In one implementation, the motion flag may be generated from a physiological signal that is different from the physiological signal on which it displayed. For example, the ML model may use depth images and/or an ECG signal to generate the detected motion and the motion flag generated based on the detected motion may be overlayed on a display of the PPG signal, etc.

Figure 15:
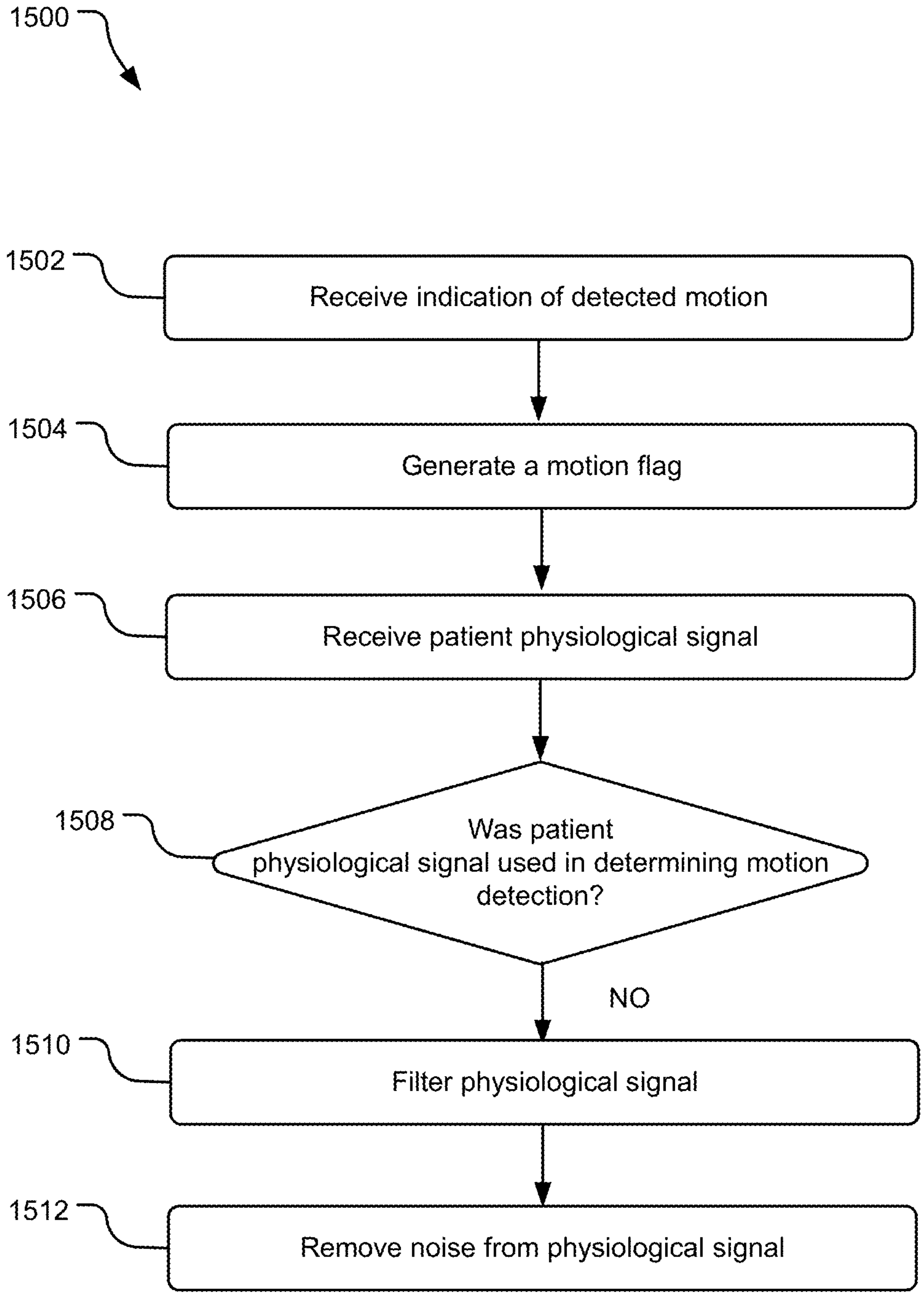
FIG. 15 illustrates alternative example operations for filtering noise from a physiological signal of the patient based on the motion of the patient as determined by the system disclosed herein.

FIG. 15 illustrates alternative operations 1500 for filtering noise from a physiological signal of the patient based on the motion of the patient as determined by the system disclosed herein. An operation 1502 receives an indication of the detected motion of the patient. For example, such an indication of the detected motion may be generated by a classifier such as the classifier 146 disclosed in FIG. 1. An operation 1506 receives a physiological signal of the patient, such as an EEG signal, an ECG signal, a PPG signal, etc. Here the physiological signal received at 1506 may be different than the physiological signal that may be used by the ML model, together with the depth images, to generate the detected motion and the motion flag. For example, the operation 1502 may generate receive indication of detected motion that is generated by an ML model using depth images together with a PPG signal, whereas the physiological signal received at operation 1506 may be the EEG signal. Subsequently, an operation 1510 may filter the EEG signal based on the value of the detected motion that was generated using depth images and/or a PPG signal. Such filtering may include adjusting the amplitude of the displayed EEG based on the amplitude of the detected motion of the patient, etc. In one implementation, an operation 1512 may remove noisy portions of the EEG signal based on the amplitude of the detected motion of the patient.

Figure 16:
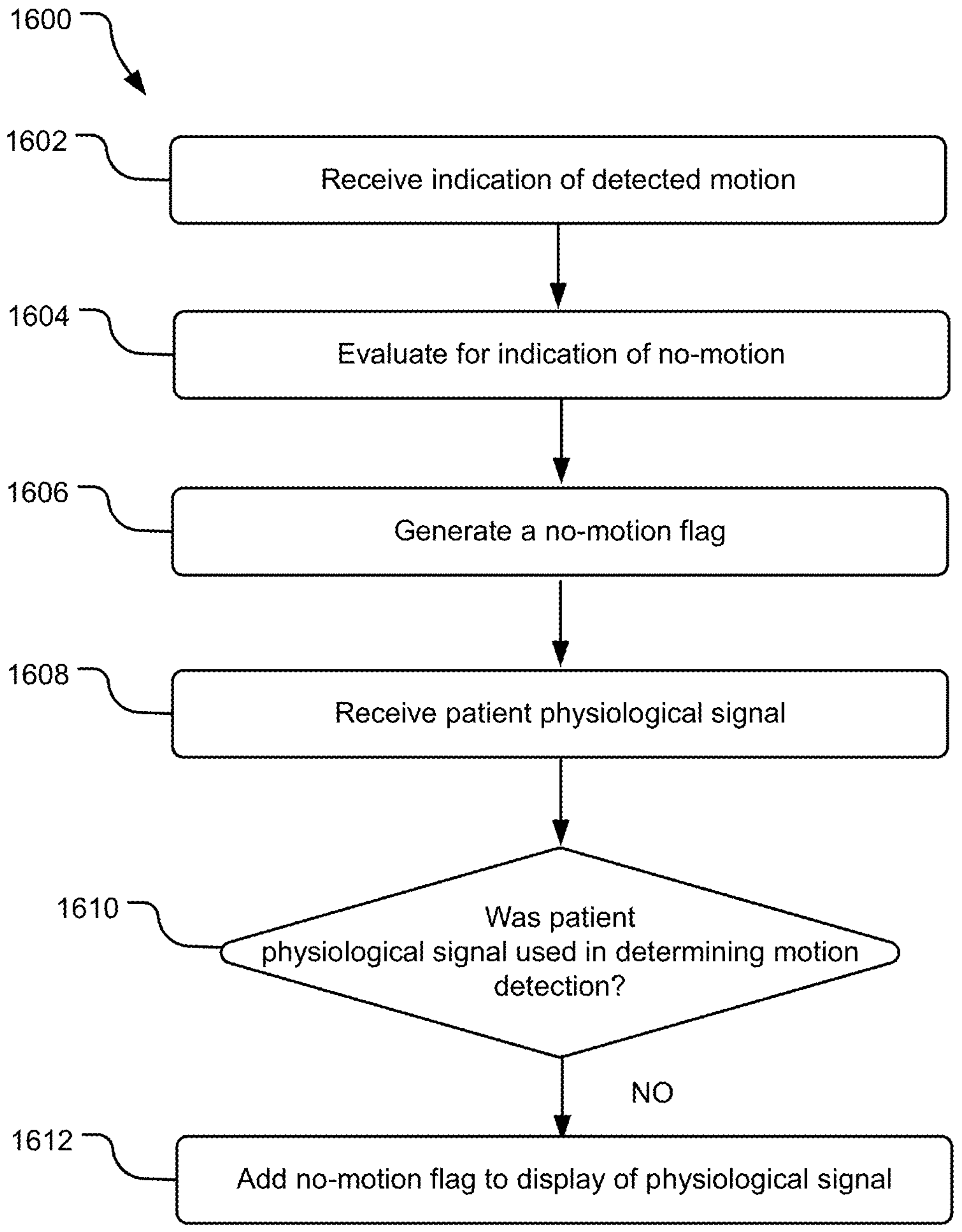
FIG. 16 illustrates alternative example operations for generating and displaying a no-motion flag on a display of a physiological signal of the patient based on the motion of the patient as determined by the system disclosed herein.

FIG. 16 illustrates alternative operations 1600 for generating and displaying a no-motion flag on a display of a physiological signal of the patient based on the motion of the patient as determined by the system disclosed herein. Specifically, the operations 1600 monitors the detected motion output from the classifier 146 to determine lack of motion by the patient for an extended period of time. For example, the operation 1600 may determine a no-motion state for the patient when no motion is detected for more than a few minutes when the patient is awake or for more than a few hours when the patient is asleep. Such extended lack of motion may indicate complications such as over-sedation, lethargy, etc. Subsequently, such detection of non-motion is used to generate a no-motion flag that may be added to the display of other physiological parameter such as display of the respiratory rate of the patient, an ECG chart of the patient, a PPG chart of the patient, etc.

An operation 1602 receives an indication of the detected motion of the patient. For example, such an indication of the detected motion may be generated by a classifier such as the classifier 146 disclosed in FIG. 1. Subsequently, an operation 1604 evaluates the output of the classifier to see if there is an indication of no-motion for the patient. For example, the operation 1604 may determine such existence of no-motion if the amplitude of the detected motion signal is below a threshold level for an elongated period of time. If so, an operation 1606 generates a no-motion flag. Here the no-motion flag may be indicative of an unusual condition for the patient and therefore, it may be useful to be displayed on top of a display of a physiological signal such as the EEG signal, etc. An operation 1608 receives a physiological signal of the patient, such as an ECG signal, a PPG signal, etc. Subsequently, at operation 1610 the no-motion flag that is determined based on the detected motion may be displayed on a display of the PPG signal.

Figure 17:
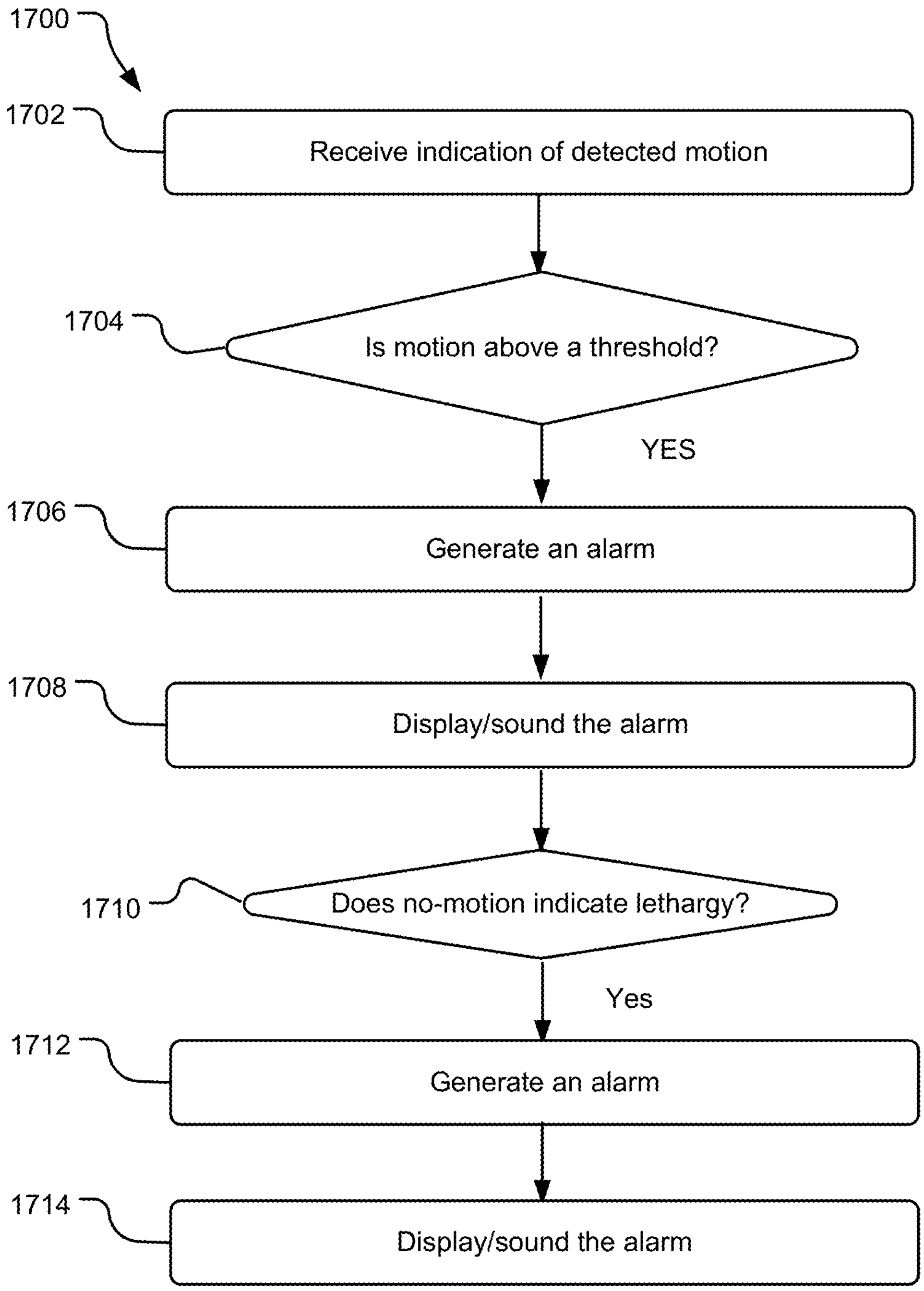
FIG. 17 illustrates example operations for modifying an alarm signal based on motion of the patient as determined by the system disclosed herein.

FIG. 17 illustrates operations 1700 for modifying an alarm signal based on the detected motion of the patient as determined by the system disclosed herein. An operation 1702 receives an indication of the detected motion of the patient. For example, such an indication of the detected motion may be generated by a classifier such as the classifier 146 disclosed in FIG. 1. Subsequently, an operation 1704 may determine if the motion above a threshold level. If so, an operation 1706 may generate an alarm and an operation 1708 may display the alarm on the physiological signal of the patient or sound the alarm.

However, if the detected motion is not above the threshold, an operation 1710 may determine if the detected motion signal indicates lack of normal or expected motion by the patient for over a threshold time period. If so, an operation 1712 may generate an alarm and an operation 1714 may display the alarm on the physiological signal of the patient or sound the alarm. However, if the detected motion signal indicates lack of normal or expected motion by the patient for over a threshold time period, there is no need for display of an alarm and therefore, no action is taken at operation 1722.

The implementations described herein are implemented as logical steps in one or more computer systems. The logical operations may be implemented (1) as a sequence of processor-implemented steps executing in one or more computer systems and (2) as interconnected machine or circuit modules within one or more computer systems. The implementation is a matter of choice, dependent on the performance requirements of the computer system being utilized. Accordingly, the logical operations making up the implementations described herein are referred to variously as operations, steps, objects, or modules. Furthermore, it should be understood that logical operations may be performed in any order, unless explicitly claimed otherwise or a specific order is inherently necessitated by the claim language.

The above specification, examples, and data provide a complete description of the structure and use of exemplary embodiments of the invention. Since many implementations of the invention can be made without departing from the spirit and scope of the invention, the invention resides in the claims hereinafter appended. Furthermore, structural features of the different embodiments may be combined in yet another implementation without departing from the recited claims.

What is claimed is:

1. A method of monitoring motion, comprising:

receiving, by a processor from a depth camera, a video stream, the video stream comprising a sequence of depth images of at least a portion of a patient, each depth image represented by a plurality of pixels, each pixel representing a depth between the depth camera and a point on at least the portion of the patient;

dividing the video stream into a plurality of temporal video sequences, each of the temporal video sequences having a plurality of temporal frames;

computing a plurality of depth difference frames based on the plurality of temporal frames, each depth difference frame representing at least one depth difference of at least one pixel between at least two temporal frames;

generating a matrix of depth difference frames;

deriving a plurality of input features over time based on the matrix of depth difference frames, the plurality of input features being indicative of an amount of movement of the patient over one or more ranges or scales;

determining a machine learning (ML) input feature matrix based on the plurality of input features; and training an ML model using the ML input feature matrix to classify motion of the patient.

2. The method of claim 1, wherein generating the matrix of depth difference frames comprises:

determining, at a first point in time, a first temporal median of a first plurality of temporal frames preceding the first point in time, determining, at a second point in time, a second temporal median of a second plurality of temporal frames preceding the second point in time, wherein the second point in time is subsequent to the first point in time; and generating a depth difference frame based on the first temporal median and the second temporal median.

3. The method of claim 1, wherein determining the ML input feature matrix further comprises determining a time series comprising a fraction of all non-null pixels within the matrix of depth difference frames.

4. The method of claim 1, wherein determining the ML input feature matrix further comprises determining a time series comprising a number of pixels within the matrix of depth difference frames with a depth difference greater than a threshold depth difference.

5. The method of claim 4, wherein the threshold depth difference is 3 mm.

6. The method of claim 1, wherein determining the ML input feature matrix further comprises determining a time series comprising a sum of depth differences of pixels within the matrix of depth difference frames with a depth difference greater than a threshold depth difference.

7. The method of claim 1, wherein determining the ML input feature matrix further comprises determining a time series comprising a sum of depth differences of pixels within the matrix of depth difference frames with a depth difference within a threshold depth difference range.

8. The method of claim 1, wherein generating the matrix of depth difference frames comprises denoising the depth difference frames by at least one of (a) performing spatial median filtering of the depth difference frames, (b) removing depth differences higher than a threshold depth difference from the depth difference frames, or (c) removing area based connected components from the depth difference frames.

9. The method of claim 1, further comprising:

inputting a real-time matrix of depth difference frames into the trained ML model to identify an area of motion by the patient; and super-imposing the area of motion by the patient on a time-series of a physiological signal of the patient.

10. The method of claim 9, further comprising modifying a display of the physiological signal of the patient based on the identified area of motion by a patient.

11. The method of claim 1, further comprising:

inputting a real-time matrix of depth difference frames into the trained ML model to detect motion by a patient;

generating a motion flag corresponding the detected motion; and displaying the motion flag with a display of a physiological signal of the patient.

12. The method of claim 1, further comprising:

inputting a real-time matrix of depth difference frames into the trained ML model to detect motion by the patient;

analyzing the detected motion to determine a period of lack of motion;

generating a no-motion flag based on the period of lack of motion; and displaying the no-motion flag with a display of a physiological signal of the patient.

13. In a computing environment, a method performed at least in part on at least one processor, the method comprising:

receiving, by a processor from a depth camera, a video stream, the video stream comprising a sequence of depth images of at least a portion of a patient, each depth image represented by a plurality of pixels, each pixel representing a depth between the depth camera and a point on at least the portion of the patient;

dividing the video stream into a plurality of temporal video sequences, each of the temporal video sequences having a plurality of temporal frames;

computing a plurality of depth difference frames based on the plurality of temporal frames, each depth difference frame representing at least one depth difference of at least one pixel between at least two temporal frames;

generating a matrix of depth difference frames;

deriving a plurality of input features over time based on the matrix of depth difference frames, the plurality of input features being indicative of an amount of movement of the patient over one or more ranges or scales;

determining a machine learning (ML) input feature matrix based on the plurality of input features; and training a machine learning model using the ML input feature matrix to classify motion of the patient.

14. The method of claim 13, wherein generating the matrix of depth difference frames comprises:

determining, at a first point in time, a first temporal median of a first plurality of temporal frames preceding the first point in time, determining, at a second point in time, a second temporal median of a second plurality of temporal frames preceding the second point in time, wherein the second point in time is subsequent to the first point in time, and generating a depth difference frame based on the first temporal median and the second temporal median.

15. The method of claim 13, further comprising:

inputting a real-time matrix of depth difference frames into the trained machine learning model to identify an area of motion by the patient; and super-imposing the area of motion by the patient on a time-series of a physiological signal of the patient.

16. The method of claim 13, wherein determining the ML input feature matrix further comprises determining a time series comprising fraction of all non-null pixels within the matrix of depth difference frames.

17. The method of claim 16, wherein determining the ML input feature matrix further comprises determining a time series comprising a number of pixels within the matrix of depth difference frames with a depth difference greater than a threshold depth difference.

18. A physical article of manufacture including one or more tangible computer-readable storage media, encoding computer-executable instructions for executing on a computer system a computer process to provide a system for contextualizing a patient physiological signal using machine learning, the computer process comprising:

receiving, by a processor from a depth camera, a video stream, the video stream comprising a sequence of depth images of at least a portion of a patient, each depth image represented by a plurality of pixels, each pixel representing a depth between the depth camera and a point on at least the portion of the patient;

dividing the video stream into a plurality of temporal video sequences, each of the temporal video sequences having a plurality of temporal frames;

computing a plurality of depth difference frames based on the plurality of temporal frames, each depth difference frame representing at least one depth difference of at least one pixel between at least two temporal frames;

generating a matrix of depth difference frames, wherein generating each depth difference frame includes:

determining, at a first point in time, a first temporal median of a first plurality of temporal frames preceding the first point in time, determining, at a second point in time, a second temporal median of a second plurality of temporal frames preceding the second point in time, wherein the second point in time is subsequent to the first point in time, and generating a depth difference frame based on the first temporal median and the second temporal median;

deriving a plurality of input features over time based on the matrix of depth difference frames, the plurality of input features being indicative of an amount of movement of the patient over one or more ranges or scales;

determining a machine learning (ML) input feature matrix based on the plurality of input features;

training a machine learning model using the ML input feature matrix to classify motion of the patient; and determining a physiological parameter based on the physiological signal and the classified motion of the patient.

19. The physical article of manufacture of claim 18, wherein the computer process further comprises:

inputting a real-time matrix of depth difference frames into the trained machine learning model to identify an area of motion by the patient; and super-imposing the area of motion by the neonatal patient on a time-series of the physiological signal of the neonatal patient.

20. The physical article of manufacture of claim 19, wherein the computer process further comprises modifying a display of the physiological signal of the neonatal patient based on the identified area of motion by the patient.

* * * * *